US008513407B2

(12) United States Patent
Oreste et al.

(10) Patent No.: US 8,513,407 B2
(45) Date of Patent: Aug. 20, 2013

(54) PROCESS FOR THE PREPARATION OF N-ACYL-(EPI)K5-AMINE-O-SULFATE-DERIVATIVES AND PRODUCTS THUS OBTAINED

(75) Inventors: Pasqua A. Oreste, Milan (IT); Giorgio Zoppetti, Milan (IT)

(73) Assignee: GLYCORES 2000 S.r.l., Milan (IT)

( * ) Notice: Subject to any disclaimer, the term of this patent is extended or adjusted under 35 U.S.C. 154(b) by 1013 days.

(21) Appl. No.: 12/120,167

(22) Filed: May 13, 2008

(65) Prior Publication Data
US 2009/0005341 A1 Jan. 1, 2009

Related U.S. Application Data

(63) Continuation-in-part of application No. 10/518,303, filed as application No. PCT/IB03/02339 on Jun. 17, 2003, now abandoned, application No. 12/120,167, which is a continuation-in-part of application No. 10/582,687, filed as application No. PCT/IB2004/004128 on Dec. 15, 2004, now Pat. No. 7,812,151.

(30) Foreign Application Priority Data

| Jun. 18, 2002 | (IT) | MI2002A1345 |
| Jun. 18, 2002 | (IT) | MI2002A1346 |
| Aug. 27, 2002 | (IT) | MI2002A1854 |
| Dec. 17, 2003 | (IT) | MI2003A2498 |

(51) Int. Cl.
*C08B 37/00* (2006.01)

(52) U.S. Cl.
USPC ........................................ 536/55.1; 536/55.3

(58) Field of Classification Search
USPC ................................................. 536/55.1, 55.3
See application file for complete search history.

(56) References Cited

U.S. PATENT DOCUMENTS

| 4,369,256 A | 1/1983 | Casu et al. |
| 4,411,796 A | 10/1983 | Casu et al. |
| 5,110,918 A | 5/1992 | Casu et al. |
| 5,314,876 A | 5/1994 | Lormeau et al. |
| 5,550,116 A | 8/1996 | Lormeau et al. |
| 5,958,899 A | 9/1999 | Zoppetti et al. |
| 6,162,797 A | 12/2000 | Zoppetti et al. |
| 6,288,044 B1 | 9/2001 | Zoppetti et al. |
| 6,329,351 B1 | 12/2001 | Naggi et al. |
| 6,777,398 B2 | 8/2004 | Zoppetti et al. |
| 6,900,311 B2 | 5/2005 | Manoni et al. |
| 6,992,183 B2 | 1/2006 | Oreste et al. |
| 7,268,122 B2 | 9/2007 | Zoppetti et al. |
| 2002/0062019 A1 | 5/2002 | Oreste et al. |
| 2003/0023079 A1 | 1/2003 | Oreste et al. |
| 2003/0100534 A1 | 5/2003 | Zoppetti et al. |
| 2003/0232785 A1 | 12/2003 | Manoni et al. |
| 2004/0077848 A1 | 4/2004 | Oreste et al. |
| 2004/0146994 A1 | 7/2004 | Zoppetti et al. |
| 2005/0004358 A1 | 1/2005 | Oreste et al. |
| 2005/0009780 A1 | 1/2005 | Zoppetti et al. |
| 2005/0027117 A1 | 2/2005 | Oreste et al. |
| 2005/0142194 A1 | 6/2005 | Nocelli et al. |
| 2005/0215518 A1 | 9/2005 | Oreste et al. |
| 2005/0245736 A1 | 11/2005 | Oreste et al. |
| 2005/0256079 A1 | 11/2005 | Oreste et al. |
| 2006/0014718 A1 | 1/2006 | Oreste et al. |
| 2006/0281152 A1 | 12/2006 | Zoppetti et al. |
| 2007/0155694 A1 | 7/2007 | Oreste et al. |
| 2008/0146793 A1 | 6/2008 | Oreste et al. |
| 2009/0005341 A1 | 1/2009 | Oreste et al. |
| 2009/0105192 A1 | 4/2009 | Oreste et al. |

FOREIGN PATENT DOCUMENTS

| EP | 0489647 | 6/1992 |
| EP | 0544592 | 6/1993 |
| WO | 97/43317 | 11/1997 |
| WO | 98/09636 | 3/1998 |
| WO | 98/34958 | 8/1998 |
| WO | 01/72848 | 10/2001 |
| WO | 02/50125 | 6/2002 |
| WO | 02/068477 | 9/2002 |
| WO | 03/106503 | 12/2003 |

OTHER PUBLICATIONS

Vann et al. Eur. J. Biochem., 1981, 116, p. 359-364.*
Definition of true, Free Merriam-Webster Dictionary, http://www.merriam-webster.com/dictionary/true, accessed online on Jun. 18, 2013.*
Jacobsson et al. "Identification of N-sulphated disaccharide units in heparin-like polysaccharides" Biochem. J. 179:77-87 (1979).
Kusche et al. "Biosynthesis of heparin" Biochem. J. 275:151-158 (1991).
Naggi et al. "Toward a biotechnological heparin through combined chemical and enzymatic modification of the *Escherichia coli* K5 polysaccharide" Sem. Thromb. Hemostas. 27:437-443 (2001).
Int'l Search Report for PCT/IB2003/002339 mailed Nov. 5, 2003, five pages.
Int'l Search Report for PCT/IB2004/004128 mailed Jun. 24, 2005, three pages.

* cited by examiner

*Primary Examiner* — Shaojia Anna Jiang
*Assistant Examiner* — Jonathan S Lau
(74) *Attorney, Agent, or Firm* — Nixon & Vanderhye PC

(57) ABSTRACT

A new method is described for the oversulfation of (epi)K5-N-sulfates to obtain (epi)K5-amine-O-oversulfates at extremely high degree of sulfation and for the transformation of these intermediates into new N-acyl-(epi)K5-amine-O-oversulfates basically free of activity on the coagulation parameters and useful in the cosmetic or pharmaceutical field. Also described are pharmaceutical compositions containing, as one of their active ingredients, an (epi)K5-amine-O-oversulfate.

30 Claims, 9 Drawing Sheets

PROCESS FOR THE PREPARATION OF N-ACYL-(EPI)K5-AMINE-O-SULFATE-DERIVATIVES AND PRODUCTS THUS OBTAINED

CROSS REFERENCE TO RELATED APPLICATIONS

This is a continuation in-part of application Ser. No. 10/518,303 filed on 26 May 2005; which is the U.S. national stage of Appln. No. PCT/IB2003/002339 filed on 17 Jun. 2003; which claims priority benefit of Italian Appln. Nos. MI2002A001345 filed on 18 Jun. 2002, MI2002A001346 filed on 18 Jun. 2002, and MI2002A001854 filed on 27 Aug. 2002. This is also a continuation in-part of application Ser. No. 10/582,687 filed on 13 Jun. 2006; which is the U.S. national stage of Appln. No. PCT/IB2004/004128 filed on 15 Dec. 2004; which claims priority benefit of Italian Appln. No. MI2003A002498 filed on 17 Dec. 2003.

FIELD OF THE INVENTION

The present invention concerns new derivatives of K5 polysaccharide with a high degree of sulfation, a process for their preparation, new highly O-sulfated intermediates useful in their synthesis and pharmaceutical compositions containing said derivatives of K5 polysaccharide as active ingredients basically free of activity on coagulation.

In particular, the invention refers to derivatives of K5 polysaccharide obtained starting with a K5 polysaccharide, previously N-deacetylated, N-sulfated, optionally depolymerized or optionally at least 20% C5-epimerized and optionally depolymerized, by O-oversulfation in suitable conditions and subsequent N-acylation of the free amine.

BACKGROUND OF THE INVENTION

The glycosaminoglycans such as heparin, heparan sulfate, dermatan sulfate, chondroitin sulfate and hyaluronic acid are biopolymers extracted industrially from various animal organs.

In particular, heparin, mainly obtained by extraction from the intestinal mucous membrane of pigs or from bovine lung, is a polydispersed copolymer with a molecular weight distribution from approximately 3,000 to approximately 30,000 D consisting of a chain mixture basically consisting of an uronic acid (glucuronic acid or iduronic acid) and of an amino sugar (glucosainine) linked by $\alpha$-1→4 or $\beta$-1→4 bonds. In heparin, the uronic unit can be O-sulfated in position 2 and the glucosamine unit is N-acetylated or N-sulfated, 6-O-sulfated and 3-O-sulfated in approximately 0.5% of the glucosainine units present.

The properties and the natural biosynthesis of heparin in mammals have been described by Lindahl et al., 1986 in Lane and Lindahl (Editors) "Heparin. Chemical and Biological Properties; Clinical Applications", Edward Arnold, London, Pages 159-190, by Lindahl et al. TIBS, 1986, 11, 221-225 and by Conrad "Heparin Binding Proteins", Chapter 2: Structure of Heparinoids. Academic Press, 1998. The biosynthesis of heparin occurs starting with its N-acetyl-heparosan precursor formed by a chain mixture consisting of the repetitive glucuronyl-$\alpha$-1→4-N-acetylglucosamine disaccharide unit. Said precursor undergoes enzymatic modifications which partially hydrolyse the N-acetyl group, substituting it with an SO3-group, epimerize the carboxy in position 5 of a part of the glucuronic units transforming them into iduronic units and introducing O-sulfate groups to get a product which, once extracted industrially, has approximately double the number of sulfate groups as regards carboxy groups per disaccharide unit. These enzymatic modifications lead, i.a. to the formation of the pentasaccharide binding for antithrombin III (ATIII), called active pentasaccharide, which is the structure necessary for the high affinity bond of heparin to ATIII and fundamental for the anticoagulant and antithrombotic activity of the heparin itself. This pentasaccharide, present inside only some of the chains which form heparin, contains a sulfated glucosamine unit in position 3 and a glucuronic acid spaced out between disaccharides containing iduronic acids.

In nature, the formation of the active pentasaccharide is made possible by the epimerization reaction of the carboxy of a part of the glucuronic units into iduronic units carried out by the glucuronyl-C5-epimerase (C5-epimerization) and by suitable sulfation which also leads to the introduction of a sulfate group on the hydroxyl in position 3 of the glucosamine. More particularly, in nature the formation of the active pentasaccharide is made possible by the fact that C5-epimerization occurs in clusters, i.e., on portions of chains, and extensively which leads to a product which contains more iduronic units than glucuronic ones. In fact, commercial heparin contains approximately 70% of iduronic units and 30% of glucuronic units.

Alongside the main anticoagulant and antithrombotic activities, heparin also exerts antilipaemic, antiproliferative, antiviral, antitumor and antimetastatic activities, but its use as a drug is hindered by the side effects due to the anticoagulant action which can cause bleeding.

It is known that the capsular K5 polysaccharide isolated from *Escherichia coli*, described by Vann et al., Eur. J. Biochem., 1981, 116, 359-364 ("Vann 1981"), is formed by a mixture of chain consisting of the repetitive disaccharide unit glucuronyl-$\beta$-1→4-N-acetyl glucosamine and therefore shows the same repetitive sequence (A)

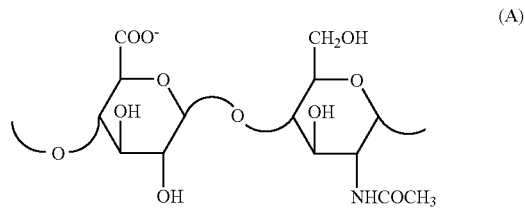

(A)

of N-acetyl-heparosan precursor of heparin. The capsular 1(5 polysaccharide, referred to hereafter as "K5 polysaccharide" or more simply "K5", was chemically modified by Lormeau et al. as described in U.S. Pat. No. 5,550,116 and by Casu et al., Carbohydrate Res., 1994, 263, 271-284 ("Casu 1994"). K5-O-sulfates having antitumor, antimetastatic, antiviral, in particular anti-HIV activities are described in EP 333243 and WO 98/34958. The K5 was also chemically and enzymatically modified in order to obtain products having in vitro biological activity on coagulation of the same type as that of heparin as extracted from animal organs (extractive heparin).

The attainment of the products having an activity on coagulation of the same type as that of extractive heparin occurs by processes which imitate that occurring in nature and all envisage the key step of C5-epimerization with D-glucuronyl C5 epimerase (Naggi et al., Seminars in Thrombosis and Hemostasis, 2001, 27, 437-443).

The processes described in IT 1230785, WO 92/17507, WO 96/14425 and WO 97/43317 utilize K5 as starting material. The K5 originating from fermentation is subjected to N-deacetylation followed by N-sulfation and on the K5-N-sulfate thus obtained C5-epimerization with C5-epimerase in solution is performed, obtained either by chromatography of a solution of microsomal enzymes from mouse mastocytoma (IT 1230 785) or from bovine liver (WO 92/17507, WO 96/14425 and WO 97/43317).

The D-glucuronyl C5 epimerase from bovine liver was purified by Campbell et al., J. Biol. Chem., 1994, 269, 26953-26958 ("Campbell 1994") who also provided its composition in amino acids and described its use in solution for the transformation of a K5-N-sulfate into the corresponding 30% epimerized product, demonstrating the formation of iduronic acid by HPLC method followed by total nitrous depolymerization to disaccharide.

The document WO 98/48006 describes the DNA sequence which codes for the D-glucuronyl C5 epimerase and a recombinant D-glucuronyl C5 epimerase, obtained from a recombinant expression vector containing said DNA, afterwards purified by Campbell et al. as shown by Jin-Ping et al., J. Biol. Chem., 2001, 276, 20069-20077 ("Jin-Ping 2001").

The complete sequence of the C5-epimerase was described by Crawford et al., J. Biol. Chem., 2001, 276, 21538-21543 ("Crawford 2001").

Beside the key step of C5-epimerization, and immediately after said epimerization, the most recent processes include an oversulfation step of the epiK5-N-sulfate, followed by controlled desulfation of the intermediate oversulfated product thus obtained, giving rise to N-desulfated products as it happens in the case of LMW-heparin (Naggi et al., Carbohydrate Res., 2001, 336, 283-290).

Thus, WO 01/72848 describes a method for the preparation of N-deacetylated N-sulfated derivatives of K5 polysaccharide, at least 40% epimerized to iduronic acid as regards the total of the uronic acids, having a molecular weight from 2,000 to 30,000, containing from 25 to 50% of high affinity chains for ATIII and having an anticoagulant and antithrombotic activity expressed as HCII/antiXa ratio from 1.5 to 4. Said document describes the oversulfation of a 40-60% epimerized K5-N-sulfate and shows that the product obtained, whose $^{13}$C-NMR is illustrated, has a sulfate group content per disaccharide unit of 2-3.5. Repeating the aforesaid oversulfation in the conditions described and examining the $^{13}$C-NMR it is ascertained that the product obtained is actually a free amine whose content of 6-O-sulfate is 80-95%, that of 3-O-sulfate on the amino sugar is 30%, but whose sulfation degree is 3.2. It is also ascertained that in the conditions of oversulfation described in WO 01/72848 a sulfation degree of more than 3.2 is not obtained.

The Italian patent application MI2001A/00397 (see also WO 02/068477), describes K5-N,O-oversulfates having a sulfation degree of more than 3.2, obtained starting from a K5 polysaccharide free of lipophilic substances or from a fraction thereof with molecular weight of approximately 5,000 by (a) N-deacetylation/N-sulfation, (b) O-oversulfation and, optionally, (c) N-resulfation.

U.S. Pat. No. 7,268,122 and Vicenzi et al., AIDS, 2003, 17, 177-181 disclose the anti-HIV activity of these K5-N,O-oversulfates. According to Vicenzi et al., the tested K5-N,O-oversulfate is more active than K5-O-oversulfate and much more active than heparin.

None of the aforesaid documents describes LMW-K5-N-sulfates, optionally 40-60% epimerized, in which $NH_2$ or acetyl groups are virtually absent.

In order to standardize the terminology and render the text more comprehensible, in the present description conventional terms or expressions will be used, in the singular or plural. In particular:

"K5" or "K5 polysaccharide" designates the capsular polysaccharide from *Escherichia coli* obtained by fermentation, i.e., a chain mixture consisting of disaccharide units (A) optionally containing a double bond at the non-reducing end as shown above, in any case prepared and purified according to the methods described in literature, in particular according to Vann 1981, according to Manzoni et al., Journal of Bioactive Compatible Polymers, 1996, 11, 301-311 ("Manzoni 1996") or according to the method described in WO 01/72848 and in WO 02/068447; it is obvious for a person skilled in the art that what is shown hereafter can be applied to any N-acetylheparosan;

"C5-epimerase" designates the D-glucuronyl C-5 epimerase, extractive or recombinant, in any case prepared, isolated and purified, in particular as described in Campbell 1994, in WO 98/48006, in Jin-Ping et al., J. Biol. Chem., 2001, 276, 20069-20077 ("Jin-Ping 2001") or in Crawford 2001;

"K5-amine" designates at least 95% N-deacetylated K5, but generally in which acetyl groups are undetectable by a current NMR apparatus;

"K5-N-sulfate" designates at least 95% N-deacetylated and N-sulfate K5 as described hereafter, but in which acetyl groups are normally undetectable with a normal NMR apparatus;

"epiK5", within the nomenclature of the glucosaminoglycans described herein, designates the K5 and its derivatives in which 20-60% of the glucuronic units are C5-epimerized to iduronic units;

"epiK5-N-sulfate" designates the K5-N-sulfate in which 20-60% of the glucuronic units is C5-epimerized to iduronic units of the type described in WO 92/17507 or WO 01/72848;

"epiK5-amine-O-oversulfate" designates all O-sulfated epiK5-amine with a sulfation degree of at least 3.4;

"N-acyl-epiK5-amine-O-oversulfate" designates an N-acylated epiK5-amine O-oversulfate, with a sulfation degree of at least 3.4;

"K5-amine-O-oversulfate" designates an O-sulfated K5-amine with a sulfation degree of at least 2.2; and "N-acyl-K5-amine-O-oversulfate" designates an N-acylated N-acyl-K5-amine-O-oversulfate with a sulfation degree of at least 2.2;

In addition:

the conventional terms and expressions herein defined above refer to K5 as isolated after fermentation, generally with a molecular weight distribution from approximately 1,500 to approximately 50,000 with a mean molecular weight of 10,000-25,000, advantageously of 15,000-25,000;

excepting specific designation of the molecular weight, the conventional terms and expressions herein defined above, when preceded by the acronym "LMW" (low molecular weight), for example LMW-K5-N-sulfate, LMW-epiK5-N-sulfate indicate low molecular weight products, having a mean molecular weight of up to 12,000;

the prefix "(epi)", which precedes "K5" in conventional terms and expressions as defined herein above, indicates that said K5-N-sulfate, K5-amine-O-oversulfate or N-acyl-K5-O-oversulfate may be non-C5-epimerized or C5-epimerized, namely that said K5-N-sulfate, K5-amine-O-oversulfate or N-acyl-K5-O-oversulfate is formed by mixtures of chains consisting of repetitive sequences of an uronic acid-glucosamine disaccharide of the type (A) above, wherein the uronic units are either all glucuronic acid units (C5-non-epimerized) or K5 polysaccharide) or contain 20-60%, of iduronic acid units (C5-epimerized). Herein below, said prefix (epi) is denoted in the formulae by the symbol " " in the 5-position of said uronic unit.

the suffix "-derivative", which follows the conventional terms and expressions as defined herein above, (a) when added to "(epi)K5-N-sulfate" globally designates (epi)K5-N-sulfates deriving from native K5 polysaccharide and fragments of said (epi)K5-N-sulfates obtained by its depolymerization; (b) when added to "(epi)K5-amine-O-oversulfate" or to "N-acyl-(epi)K5-amine-O-oversulfate", globally designates (epi)K5-amine-O-oversulfates and N-acyl-(epi)K5-amine-O-oversulfates deriving from (epi)K5-N-sulfate-derivatives; and (c) its absence means that said (epi)K5-N-sulfates, (epi)K5-amine-O-oversulfates or N-acyl-(epi)K5-amine-O-oversulfates either are derived from native K5 polysaccharide or are low molecular weight products but, in this case, the chemical name is preceded by "LMW" as defined above;

the term "approximately", referring to the molecular weight, designates the molecular weight [± the theoretical weight of a disaccharide unit, including the weight of the sodium, calculated as 461 in the case of an (epi)K5-N-sulfate-derivative] measured by viscosimetry according to Johnson et al., Carbohydrate Res., 1976, 51, 119-127 utilizing samples whose molecular weight was calculated by HPLC as the standard;

the expression "preponderant species", designates the compound which, in the mixture constituting a lmw-(epi)K5-N-sulfate, a LMW-(epi)K5-amine-oversulfate or a LMW-N-acyl-(epi)K5-amine-O-oversulfate, is the most represented type, determined by the peak of the curve of the molecular weight measured by HPLC;

unless otherwise specifically stated, "degree of sulfation" designates the $SO_3^-/COO^-$ ratio, expressible also as the number of sulfate groups per disaccharide unit, measured with the conductimetric method described by Casu et al., Carbohydrate Res., 1975, 39, 168-176 ("Casu 1975"), the same utilized in WO 01/72848;

"conditions of O-oversulfation" define an extreme O-sulfation performed for example according to the method C described by Casu 1994;

"alkyl" designates a linear or branched alkyd whereas the term "tetrabutylammonium" indicates the tetra(n-butyl) ammonium; and "functional derivative", referred to the $(C_2-C_4)$Carboxylic acids, defines functional derivatives such as halides; anhydrides; mixed anhydrides; activating esters, for example 2,2,2-trichloroethyl, t-butyl or pentachlorophenyl esters; or the free acid itself, when activated in situ for example with dicyclohexylcarbodiimide.

SUMMARY OF THE INVENTION

It has now been found that, starting from an epiK5-N-sulfate, it is possible to obtain an epiK5-amine-O-sulfate with a degree of sulfation greater than that of every other epiK5-amine-O-sulfate described in the literature, for example in WO 01/72848, by preparing the salt with a tertiary or quaternary organic base of said epiK5-N-sulfate-derivative taking care to let the reaction mixture to stand for a time period of 30-60 minutes maintaining the pH at approximately 7 with the same organic base and then treating the salt obtained with an O-sulfation reagent in the conditions of O-oversulfation. Also a LMW-epiK5-N-sulfate, when subjected to the same method of salification and of O-oversulfation, gives a LMW-epiK5-amine-O-sulfate with an extremely high degree of sulfation. In the case of such epi-K5-amine-oversulfate-derivatives the degree of sulfation is more than 3.2.

Similarly, it was found that, applying the conditions of O-oversulfation described above to a LMW-K5-N-sulfate a LMW-K5-amine-O-sulfate is obtained at a high degree of sulfation. Also a K5-N-sulfate, when subjected to the same method of salification and of O-oversulfation, gives a K5-amine-O-sulfate with a high degree of sulfation. In the case of such K5-amine-oversulfate-derivatives the degree of sulfation is more than 2.2.

In fact, it was surprisingly found that, preparing the tetrabutylammonium salt of an (epi)K5-N-sulfate-derivative in the aforesaid conditions, the salification becomes complete and, during the subsequent O-oversulfation, favors the total displacement of the sulfate group from the nitrogen atom in position 2 of the glucosamine to the oxygen atoms of the glucosamine itself, in particular to the oxygen atom in position 3, thus giving rise to (epi)K5-amine-O-sulfate-derivatives with a high degree of sulfation in which the $NH_2$ group is strictly free. The quantitative difference in sulfation degree of the derivatives epiK5 and K5 depends on their configuration which favors the sulfation of the epimerized derivatives.

It has also been found that, subjecting an (epi)K5-amine-O-oversulfate-derivative thus obtained to N-acylation, new N-acyl-(epi)K5-amine-O-sulfate-derivatives are obtained free of activity on coagulation and useful for the preparation of pharmaceutical or cosmetic compositions. By this new and versatile process it is thus possible to prepare in a reproducible manner epiK5-O-sulfate-derivatives, their N-acyl analogues, a K5-O-sulfate having a precise degree of sulfation and, above all, its derivatives of low molecular weight and their N-acyl-analogues.

Furthermore, it has been surprisingly found that N-acyl-(epi)K5-O-oversulfate-derivatives possess a very high activity against *Herpes symplex* virus and that their activity is even higher than that of the corresponding K5-N,O-oversulfates described in WO 02/068477 and in U.S. Pat. No. 7,268,122, the latter disclosing their anti-HIV activity.

Finally, it has been found that all the (epi)K5-amine-O-oversulfate-derivatives having a sulfation degree of from 2 to 4, obtained by treatment of the corresponding (epi)K5-N-sulfate-derivatives with an O-sulfation agent under O-oversulfation conditions, are substantially devoid of anticoagulant activity, have a good microbicidal activity, and thus are active ingredients for the preparation of pharmaceutical compositions. Said pharmaceutical compositions are destined to the treatment of infection of microbial, in particular viral, origin. This finding is surprising because literature does not disclose any biological activity of K5 polysaccharide derivatives wherein the amino groups of the glucosamine subunits are fee.

DETAILED DESCRIPTION OF SPECIFIC EMBODIMENTS

Figure 1:
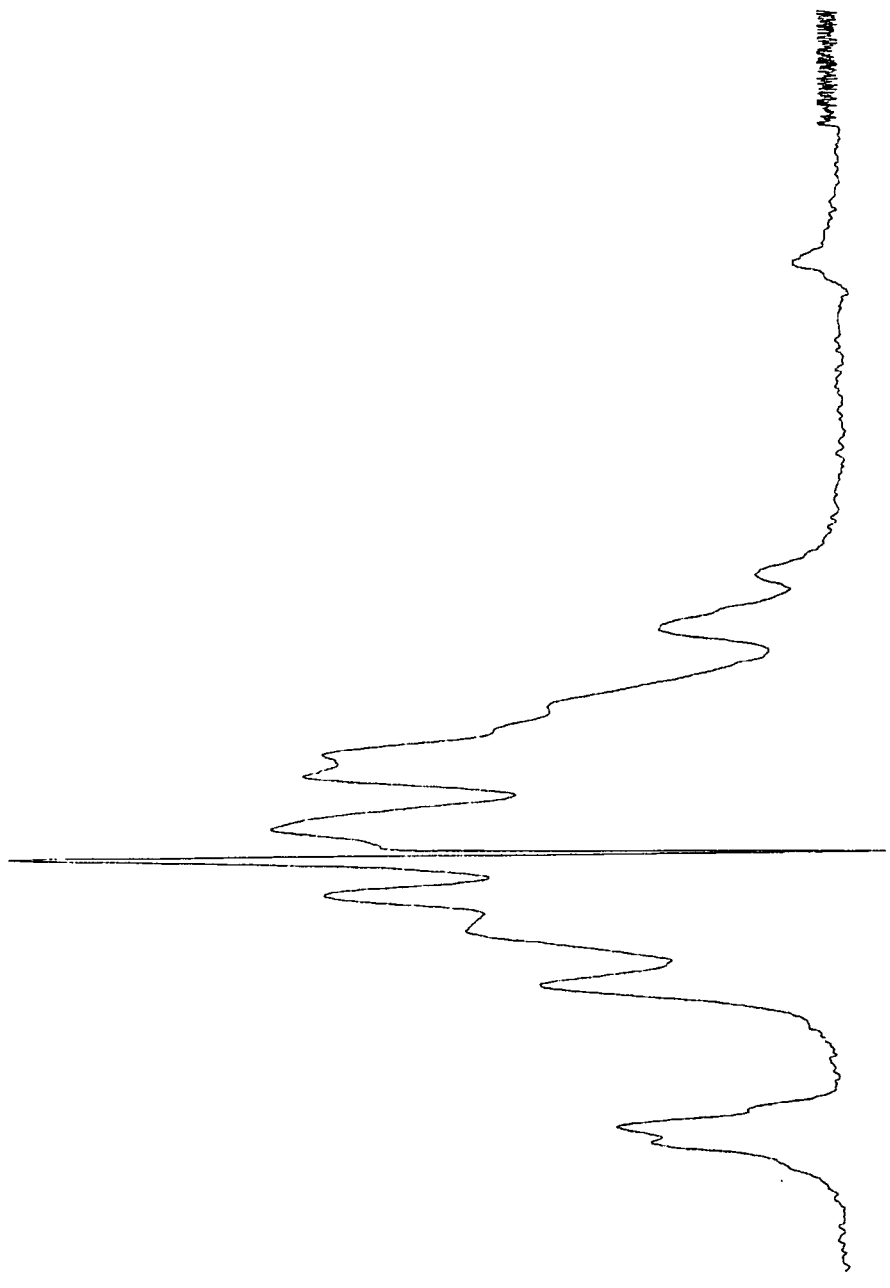
FIG. 1 shows the $^1$H-NMR spectrum of the K5-amine-O-oversulfate of Example 3(a) with a sulfate/carboxyl ratio of 2.87.

Thus, according to one of its aspects, the present invention provides a process for the preparation of N-acyl-(epi)K5-amine-O-oversulfate-derivatives, characterized in that (a) an (epi)K5-N-sulfate-derivative, in acidic form, is treated with a tertiary or quaternary organic base, letting the reaction mixture to stand for a time period of 30-60 minutes, maintaining the pH of the solution at a value of approximately 7 and its salt with said organic base is isolated;

(b) said organic base salt of said (epi)K5-N-sulfate-derivative is treated with an O-sulfation reagent in the conditions of O-oversulfation; and (c) the product thus obtained is treated with a functional derivative of a ($C_2$-$C_4$) carboxylic acid, the N-acyl-(epi)K5-amine-O-oversulfate-derivative thus obtained is isolated.

Generally the N-acyl-(epi)K5-amine-O-oversulfate-derivative is isolated in sodium salt form and optionally said sodium salt is transformed into another chemically or pharmaceutically acceptable salt.

In this context, the term "chemically acceptable" refers to a cation usable in chemical synthesis, such as the ions sodium, ammonium, ($C_1$-$C_4$)tetraalkylammonium, or for the purification of the product, whereas "pharmaceutically acceptable" is self-explanatory.

Advantageous cations are those derived from alkaline metals, alkaline-earth metals, ammonium, ($C_1$-$C_4$)tetraalkylammonium, aluminum and zinc. Preferred cations are the sodium, calcium and tetrabutylammonium ions.

According to an advantageous procedure, the step (a) is carried out by passing a solution of the sodium salt of the (epi)K5-N-sulfate-derivative, i.e., of K5 polysaccharide, previously N-deacetylated, N-sulfated preferably 100%, optionally 20-60% C5-epimerized and optionally depolymerized with nitrous acid, having a mean molecular weight from approximately 1,000 to approximately 25,000, advantageously from approximately 1,500 to approximately 25,000, through an acid ionic exchange resin, for example of the type IR-120 H$^+$, collecting the eluate including also the washing water of the resin and neutralizing the eluate with tertiary or quaternary organic base, preferably with an aqueous solution of tetrabutylammonium hydroxide. The solution is let to stand for 1 hour, maintaining its pH at approximately 7 (i.e., trying to maintain neutrality) by addition of the same tertiary or quaternary organic base, preferably an aqueous solution of tetrabutylammonium hydroxide, and the salt thus obtained is recovered by lyophilization. According to this advantageous embodiment, the complete formation of the tertiary or quaternary salt allows a broader oversulfation in subsequent step (b) with consequent obtainment of (epi)K5-amine-O-oversulfate-derivatives with a sulfation degree higher than 3.4, preferably from 3.55 to 3.8, and of the corresponding N-($C_2$-$C_4$)acyl-(epi)K5-amine-O-oversulfate-derivatives after step (c).

In step (b), the O-oversulfation occurs utilizing an excess of O-sulfating agent and working at a temperature from 20 to 70° C. for a time period of up to 24 hours in an aprotic polar solvent.

Advantageously, the tertiary or quaternary organic base salt of the (epi)K5-N-sulfate-derivative, i.e., of K5 polysaccharide, previously N-deacetylated, N-sulfated preferably 100%, optionally 20-60% C5-epimerized and optionally depolymerized with nitrous acid, having a mean molecular weight from approximately 1,500 to approximately 25,000 as isolated in step (a), is dissolved in dimethylformamide and treated with 2-100 moles of an O-sulfation reagent for every free hydroxyl at a temperature of 40-60° C. for 10-20 hours. As O-sulfation reagent the pyridine.SO$_3$ adduct in a quantity of 2.5-5 moles, preferably 2.5-4 moles per free hydroxyl per disaccharide is advantageously used and the reaction is advantageously carried out at 50-60° C., preferably at 55° C. overnight. The product obtained upon termination of the reaction is isolated by the addition of 0.1-1 volume of water and neutralization, preferably with sodium hydroxide, precipitation with a saturated sodium chloride solution in acetone, filtration and possible ultrafiltration.

The product thus obtained is generally the sodium salt of an (epi)K5-amine-O-oversulfate-derivative having a glucuronic and iduronic acids content as shown above. When the oversulfation reaction is performed on the tertiary or quaternary base salt, preferably on the tetrabutylammonium salt of an epiK5-N-sulfate-derivative having a mean molecular weight from approximately 1,000 to approximately 25,000, advantageously from approximately 1,500 to approximately 25,000 in which the iduronic acid is 20-60% of the total of the uronic acids, an epiK5-amine-O-oversulfate-derivative is obtained having a mean molecular weight of from approximately 3,500 to approximately 40,000, advantageously from approximately 4,500 to approximately 40,000, and a sulfation degree of at least 3.4, advantageously of at least 3.5, more advantageously from 3.55 to 4, preferably from 3.55 to 3.8.

When the oversulfation reaction is performed on the salt of the tertiary or quaternary base, preferably on the tetrabutylammonium salt of a K5-N-sulfate-derivative having a mean molecular weight from approximately 1,500 to approximately 25,000, a K5-amine-O-oversulfate-derivative is obtained having a mean molecular weight from approximately 3,500 to 40,000, advantageously from approximately 4,500 to approximately 40,000 and a sulfation degree of at least 2.2, advantageously from 2.2 to 3 or from 2.3 to 3, more advantageously from 2.5 to 3, preferably from 2.7 to 2.9. Preferably, the product thus obtained comes from a LMW-K5-N-sulfate and is preferably the sodium salt of a LMW-K5-amine-O-oversulfated having a degree of sulfation from 2.3 to 3, The mean molecular weight of such product can be of from approximately 3,500 to approximately 11,000.

The sodium salt thus obtained can be converted into another salt. By way of example, calcium ionic exchange can be performed working with an ultrafiltration membrane.

In step (c), the (epi)K5-amine-O-oversulfate-derivative with a high degree of sulfation is N-acylated utilizing the known literature methods.

The N-acylation is performed by making the (epi)K5-amine-O-oversulfate-derivative originating from step (b) to react with a functional derivative of a mono or dicarboxylic acid containing from 2 to 4 carbon atoms in hydroalcoholic solution at a temperature of approximately 4° C. As functional derivatives of said ($C_2$-$C_4$) carboxylic acids, preferably of acetic, propionic, malonic, or succinic acid or of mono esters, in particular methyl or ethyl, of the latter, one can use the anhydride, the chloride, a mixed anhydride or an active ester. The product obtained, an N-(C2-C4)acyl-(epi)K5-amine-O-oversulfate-derivative, is neutralized with a base, preferably sodium hydroxide, and then isolated by ultrafiltration and precipitation with a saturated sodium chloride solution in acetone. Optionally the step of N-acylation is repeated until obtaining total substitution or however more than 95%. The N-acyl-(epi)K5-amine-O-oversulfates, in particular the N-acetyl-, N-(2-carboxy)acetyl-, N-(2-methoxycarbonyl)acetyl-, N-(2-ethoxycarbonyl)acetyl-, N-propionyl-, N-(3-carboxy) propionyl-, N-(3-methoxycarbonyl)propionyl-, N-(3-ethoxycarbonyl)propionyl-(epi)K5-amine-O-oversulfates are thus obtained.

Alternatively, when (epi)K5-N,O-oversulfate-derivatives are readily available (see WO 02/068477 and WO 03/106504), the (epi)K5-amine-O-oversulfate-derivatives and, consequently, the N-($C_2$-$C_4$)acyl-(epi)K5-amine-O-oversulfate-derivatives deriving therefrom may be prepared starting from said (epi)K5-N,O-oversulfate-derivatives. Accordingly, the starting (epi)K5-N,O-oversulfate-derivative is N-desulfated by the methods known in the art, for example by bringing the pH of an aqueous solution of the substrate to a very acidic value by a strong acid such as hydrochloric acid and heating the solution at 40-60° C. for a period of time allowing the complete N-desulfation, whereby the corresponding (epi)K5-amine-O-oversulfate-derivative is obtained and may be isolated. Said (epi)K5-amine-O-oversulfate-derivative may be made to react with an activated ($C_2$-$C_4$)carboxylic acid under the condition of the optional step (c) above in order to isolate the corresponding N-($C_2$-$C_4$)acyl-(epi)K5-amine-O-oversulfate-derivative.

The new N-acyl-(epi)K5-amine-O-oversulfate-derivatives thus obtained are generally in their sodium salt forms. Said sodium salt can be converted into another chemically or pharmaceutically acceptable salt. Particularly advantageous salts are those of alkaline metals, alkaline-earth metals, of ammonium, tetra($C_1$-$C_4$)alkylammonium, aluminum and zinc. The salts of sodium, calcium and tetrabutylammonium are preferred.

Unlike the process described in WO 98/34958, which consists of a sulfation in heterogeneous phase of the K5 sodium salt to obtain K5-O-sulfates (according to the terminology used herein "N-acetyl-K5-amine-O-sulfates") with a degree of sulfation from 0.5 to 4 and which has to resort to the use of chlorosulfonic acid to obtain derivatives of low molecular weight in an uncontrolled manner, the process of the present invention is extremely versatile. In fact, it allows the preparation of N-acyl-K5-amine-O-oversulfates of every type in very high yields, with easily controllable reactions. In particular, the process of the present invention allows the preparation of N-acyl-K5-amine-O-oversulfates otherwise unobtainable, like the epimerized C-5 derivatives, the N-acylated derivatives with an acyl different from the acetyl present in the native K5 and the derivatives of low molecular weight. Besides, unlike the method described in WO 98/34958, the process of the present invention allows the attainment of LMW-K5-O-sulfates in controlled manner in order to obtain the desired mean molecular weight and, above all, a well defined sulfation degree which can range from 2.3 to 3 but which can regularly be 2.7-2.9. Finally, all the products of the process of the present invention, in particular the free intermediate amines and the N-acyl-K5-amine-O-oversulfates are useful active ingredients for pharmaceutical or cosmetic compositions.

The starting materials of step (a) are (epi)K5-N-sulfate-derivatives known in literature or their moieties, or LMW-(epi)K5-N-sulfates prepared by nitrous depolymerization of the corresponding (epi)K5-N-sulfates.

The starting (epi)K5-N-sulfate-derivatives have a mean molecular weight from approximately 1,000 to approximately 25,000, advantageously from approximately 1,500 to approximately 25,000. Preferably, an (epi)K5-N-sulfate having a mean molecular weight between 10,000 and 25,000 or LMW-(epi)K5-N-sulfate having a mean molecular weight from approximately 1,500 to approximately 12,000, advantageously from approximately 1,500 to approximately 8,000, preferably from approximately 1,500 and approximately 7,500 is used as starting material.

A LMW-epiK5-N-sulfate having an iduronic units content of approximately 20%, obtained by N-deacetylation, N-sulfation and C5-epimerization of a moiety of 1(5 having a mean molecular weight of 5,000 is described in WO 92/17507, but this product contains a high percentage of acetyl groups.

An epiK5-N-sulfate particularly advantageous as starting material is that obtained by epimerization of a K5-N-sulfate virtually free of acetyl groups in turn prepared from particularly pure K5 polysaccharide, in particular not containing lipophilic substances, described in WO 02/068477.

The low molecular weight C5-epimerized K5-N-sulfates having a higher content of iduronic units, in particular 40-60%, preferably 50-55%, are instead particularly advantageous new products as starting materials in the preparation of the N-substituted epiK5-amine-O-oversulfate-derivatives of the present invention.

The LMW-epiK5-N-sulfates can also be obtained by C5-epimerization of the corresponding LMW-K5-N-sulfates, preferably when their mean molecular weight is more than 4,000. The LMW-K5-N-sulfates virtually free of acetyl groups are all new products preparable by fractionation or, preferably, by depolymerization of a K5-N-sulfate free of acetyl groups. The K5-N-sulfate is well known in literature and is described in documents cited herein above to illustrate the state of the art. The aforesaid starting material is invariably obtained by N-deacetylation of K5 and subsequent N-sulfation of the K5-amine thus obtained. However, it was ascertained that the preparation of a K5-N-sulfate virtually free of acetyl or $NH_2$ groups is rendered easier if the K5 polysaccharide from which it is prepared is particularly pure, in particular if it does not contain lipophilic substances. It is therefore preferred, according to the present invention, to use a starting K5-N-sulfate prepared from a purified K5 as described in WO 02/068477. Said K5-N-sulfate, whose $^{13}$C-NMR spectrum does not show traces of N-acetyl or $NO_2$ groups is also described in WO 02/068477.

The new LMW-epiK5-N-sulfates as shown above are prepared by a process characterized in that a K5-N-sulfate is subjected, in any order, (i) to C5-epimerization with a D-glucuronyl C5-epimerase that is isolated, purified and in solution or immobilized on a solid support, at a pH of approximately 7, at a temperature of approximately 30° C. and for a time period of 12-24 hours in the presence of at least one bivalent ion selected among calcium, magnesium, barium and manganese; and (ii) to nitrous depolymerization optionally followed by reduction, normally with sodium borohydride.

The expression "in any order" indicates that the process can be indifferently carried out both in the direction (i)-(ii), i.e., in the sequence above indicated, and in the reverse direction, i.e., also in the direction (ii)-(i), subjecting the K5N-sulfate at first to the nitrous depolymerization reaction, optionally followed by reduction with sodium borohydride, and afterwards to the C5-epimerization in the aforesaid conditions. The preferred order is in the direction (i)→(ii). The sequence (ii)-(i) is preferably utilized starting from LMW-K5-N-sulfates having a mean molecular weight of more than 4000, preferably from approximately 6,000. For example, one can determine the amounts of sodium nitrite which, starting from 1 g of epiK5-N-sulfate, allow the attainment of a ILMW-epiK5-N-sulfate with a molecular weight of more than 4,000, in particular of at least 6,000, so as to obtain useful intermediates for the preparation of LMWepiK5-N,O-oversulfates. In fact, in this case, in step (ii) the percentage of optimum epimerization is obtained.

According to a preferential aspect of the invention, the C5-epimerase is immobilized on an inert solid support.

The C5-epimerase, preferably recombinant, isolated and purified for example according to Campbell 1994, WO 98/48006, Jin-Ping 2001 or Crawford 2001, is immobilized on an inert support in the presence of the substrate, i.e., in the presence of starting K5-N-sulfate-derivative or in the presence of LMW-K5-N-sulfate, advantageously having a mean molecular weight of more than 4,000, preferably of at least 6,000. The immobilization is performed according to conventional methods, for example as described in WO 01/72848. The C-5 epimerization reaction is carried out by recirculating 20-1,000 ml of a solution of 25 mM HEPES at a pH1 of approximately 7 containing 0.001-10 g of substrate (K5-N-sulfate or LMW-K5-N-sulfate, preferably with a molecular weight of more than 4,000, in particular of at least 6,000) and a cation selected among calcium, magnesium, barium and manganese at a concentration between 10 and 60 mM through a column containing from $1.2 \times 10^7$ to $3 \times 10^{11}$ cpm of the immobilized enzyme, maintaining the pH at approximately 7 at approximately 30° C., at a flow of 30-220 ml/hour for a time period of 12-24 hours, advantageously of 15-24 hours.

Preferably said solution is recirculated at a flow rate of approximately 200 ml/hour overnight (15-20 hours). The product obtained is purified and separated according to known methods, for example by ultrafiltration and precipitation with ethanol. The product thus obtained consists either of epiK5-N-sulfate (and in such a case is dissolved in water and subjected to depolymerization) or of LMW-epiK5-N-sulfate (in such a case it constitutes the end product). The percentage of epimerization, in practice the amount of iduronic units as in respect of the glucuronic ones, is calculated by $^1$H-NMR according to the method described in WO 96/4425.

The nitrous depolymerization reaction is carried out according to known methods by the depolymerization of heparin, for example according to the method described in EP 37319, in WO 82/03627 or according to the method for the depolymerization of a K5-N-sulfate described in EP 544592, but starting with a K5-N-sulfate or an epiK5-N-sulfate containing from 0 to no more than 10%, preferably no more than 5%, acetyl groups. Preferably, the depolymerization, performed with sodium nitrite and hydrochloric acid on an epiK5-N-sulfate virtually free of acetyl groups, is followed by in situ reduction with sodium borohydride.

In practice, a cold aqueous solution of epiK5-N-sulfate is brought to acid pH (approximately 2) with hydrochloric acid and, still cold, treated with sodium nitrite by maintaining the temperature (approximately 4° C.) and the pH (approximately 2) constant and, upon termination of depolymerization (approximately 15-30 minutes) the solution is neutralized with sodium hydroxide and treated, still at approximately 4° C., with an aqueous solution of sodium borohydride. Upon termination of the reduction (approximately 4 hours) the excess sodium borohydride is destroyed with hydrochloric acid, the solution is neutralized with sodium hydroxide and the depolymerized (and reduced) product is isolated according to known methods, for example by straightforward precipitation with ethanol or acetone. The product obtained upon termination of the depolymerization can be either a LMW-epiK5-N-sulfate (in such case it constitutes the end product) or a LMW-K5-N-sulfate (and in such case is directly subjected to C5-epimerization as shown herein above, after isolation or also in solution without being previously isolated), in particular when it has a mean molecular weight of more than 4,000, preferably of at least 6,000, or is utilized to prepare LMW-K5-N,O-oversulfated of antiangiogenetic and antiviral activity. By appropriately controlling the depolymerization reaction, in particular utilizing different amounts of sodium nitrite/hydrochloric acid, LMW-K5-N-sulfates or LMW-epiK5-N-sulfates are obtained having a mean molecular weight in the whole interval of from approximately 1,500 to approximately 12,000, advantageously from approximately 1,500 to approximately 10,000, preferably from approximately 1,500 to approximately 7,500, calculated at the $^{13}$C-NMR spectrum through the integration of the signal attributed to the C2 of the 2,5-anhydromannitol with that of the anomeric carbon of the glucosainine inside the polysaccharide chain. According to a general procedure, starting for example from 1 g of K5-N-sulfate or of epiK5-N-sulfate, the starting product is dissolved in 100-200 ml of deionized water and thermostated at 4° C. Then an amount of sodium nitrite is added so as to obtain the mean molecular weight desired, for example from approximately 2,000 to approximately 4,000. Therefore, starting from an epiK5-N-sulfate having a molecular weight of 20,000 measured with HPLC method equipped with a BioRad BioSil 250 column and utilizing a heparin standard of known molecular weight, the preparation of such LMW-epiK5-N-sulfate will require the addition of from 330 to 480 mg of sodium nitrite dissolved in a 0.2% aqueous solution. The solution containing the epiK5-N-sulfate and the sodium nitrite, kept at 4° C., is brought to pH 2 through addition of 0.1 N HCl cooled to 4° C. It is reacted under slow agitation for 20-40 minutes, then is neutralized with 0.1 N NaOH. The product obtained is brought to room temperature and treated with reducing agent such as for example sodium borohydride (250-500 mg dissolved in 50-100 ml of water) and reacted for 4-8 hours. The excess sodium borohydride is eliminated bringing the pH to 5-5.5 with 0.1 N HCl and let to stand for a further 2-4 hours. In the end it is neutralized with 0.1 N NaOH and the product is recovered by precipitation with acetone or ethanol after having concentrated the product through evaporation at reduced pressure.

Similarly, the amounts of sodium nitrite can be determined which, starting with 1 g of K5-N-sulfate or of epiK5-N-sulfate, allow the attainment of a lmw-K5-N-sulfate or a lmw-epiK5-N-sulfate with a mean molecular weight from approximately 4,000 to approximately 12,000, advantageously from approximately 4,000 to approximately 7,500, in particular of 6,000-7,500.

The LMW-epiK5-N-sulfates thus obtained, with an iduronic acid content from 20 to 60%, advantageously from 40 to 60%, preferably of 50-55% and virtually free of $NH_2$ and N-acetyl groups, having a mean molecular weight from approximately 1,500 to approximately 12,000, advantageously from approximately 1,500 to approximately 10,000, preferably from approximately 1,500 to approximately 7,500 and their chemically or pharmaceutically acceptable salts constitute new products useful as starting materials in the preparation of particularly interesting LMW-epiK5 N,O-oversulfates, but also themselves useful as active ingredients of pharmaceutical or cosmetic compositions and constitute an additional aspect of the present invention.

Advantageously, the starting materials in the preparation of the N-acyl-(epi)K5-amine-O-oversulfate-derivatives of the present invention are (epi)K5-N-sulfate-derivatives consisting of mixture of chains in which at least 90% of said chains have the formula I

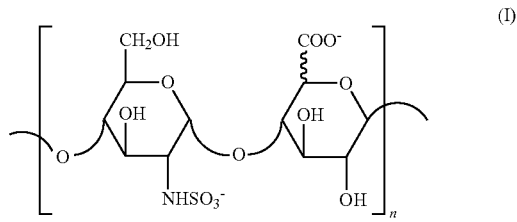

in which the glucuronic units/iduronic units ratio is from 100/0 to 40/60, n is an integer from 2 to 100, advantageously from 3 to 100, and the corresponding cation is chemically or pharmaceutically acceptable.

In particular, said starting (epi)K5-N-sulfate-derivatives are consisting of a chain mixture in which at least 90% of said chains have the aforesaid formula I, with a glucuronic units content from 100 to 40%, advantageously with a glucuronic acid content of 100% or 80-40% of glucuronic acid and 20-60% of iduronic acid, n is an integer from 2 to 100, advantageously from 3 to 100 and the corresponding cation is chemically acceptable. Preferably, the glucuronic acid content is 100% or out of the total of uronic acids 40-60% is glucuronic acid and 60-40% is iduronic acid.

Preferred starting materials are LMW-(epi)K5-N-sulfates consisting of a chain mixture in which at least 90% of said chains have the formula I in which the uronic units are all consisting of glucuronic acid or are consisting of 40-60%, preferably 50-55%, of iduronic acid, n is an integer from 2 to 20, advantageously from 3 to 15 and the corresponding cation is chemically acceptable. The epiK5-N-sulfates, prepared by C5-epimerization of K5-N-sulfates, are well known and widely described in the literature. Their preparation by C-5 epimerization of the glucuronic unit of K5-N-sulfate with a D-glucuronyl C5 epimerase was described in documents cited herein above to illustrate the state of the art, for example in WO 92/17507, WO 98/14425, WO 97/43317, WO 01/72848 and US 2002/0062019. However, according to a preferential embodiment, for the epimerization a K5-N-sulfate is used obtained from a K5 free of lipophilic substances as described in WO 02/068477 and the C5 epimerization is performed with a D-glucuronyl C5-epimerase isolated, purified and immobilized on a solid support, at a pH of approximately 7, at a temperature of approximately 30° C. and for a time period of 12-24 hours in the presence of at least one bivalent ion selected among calcium, magnesium, barium and manganese as shown above. Also the K5-N-sulfate has been illustrated herein above.

The fully N-sulfated (epi)K5-N-sulfates of low molecular weight, in particular those in which the uronic units are all in glucuronic acid and those having an iduronic units content of 40-60%, preferably 50-55%, are instead all particularly new products advantageous as starting materials in the preparation of the N-acyl-(epi)K5-amine-O-oversulfate-derivatives according to the present invention. Said starting materials are LMW-(epi)K5-N-sulfates having an iduronic acid content of 0% or 40-60% as regards the total of the uronic acids and a mean molecular weight from approximately 1,500 to approximately 12,000, advantageously from approximately 1,500 to approximately 8,000, preferably from approximately 1,500 to approximately 7,500; and their chemically or pharmaceutically acceptable salts. The distribution can range from approximately 1,000 to approximately 10,000. Said LMW-(epi)K5-N-sulfates are advantageously consisting of a chain mixture in which at least 90% of said chains have the formula I'

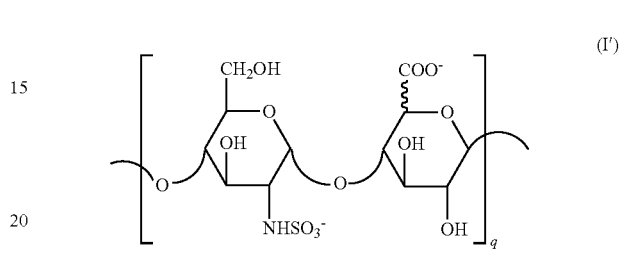

in which the uronic units are 100% consisting of glucuronic acid or 60-40% of glucuronic acid and 40-60% of iduronic acid, q is an integer from 2 to 20 and the corresponding cation is chemically or pharmaceutically acceptable.

In this con-text, the term "chemically" refers to a cation usable in chemical synthesis, such as the ions sodium, ammonium, tetra($C_1$-$C_4$) alkylammonium, or for the purification of the product.

Advantageous cations are those derived from alkaline metals, alkaline-earth metals, ammonium, tetra($C_1$-$C_4$)alkylammonium, aluminum and zinc. Preferred cations are the sodium, calcium and tetrabutylammonium ions.

Preferred starting materials are the new LMW-(epi)K5-N-sulfates consisting of a chain mixture in which the preponderant species has the formula I'a

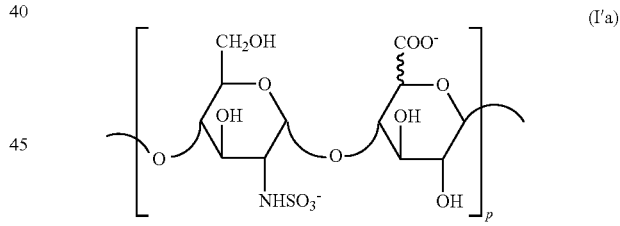

in which the uronic units are 100% consisting of glucuronic acid or 60-40% glucuronic and 40% to 60% of iduronic acid, p is an integer from 4 to 8. The mean molecular weight of these products is from approximately 2,000 to approximately 4,000 and the corresponding cation is chemically or pharmaceutically acceptable.

In particular the new LMW-(epi)K5-N-sulfates are useful starting materials consisting of a chain mixture in which at least 90% of said chains have the formula I' herein above, obtained by nitrous depolymerization of the corresponding (epi)K5-N-sulfates shown above and subsequent possible reduction for example with sodium borohydride.

The origin of these (epi)K5-N-sulfates from a step of nitrous depolymerization involves, at the reducing end of the majority of the chains in said chain mixture, the presence of a 2,5-anhydromannose unit or, in case of reduction with for example sodium borohydride, of 2,5-anhydromannitol of structure (a)

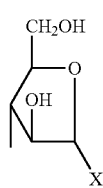
(a)

in which X represents a formyl group or a hydroxymethyl group. Therefore, the reducing end of the majority (60-70%) of the chains is actually represented by the structure (b)

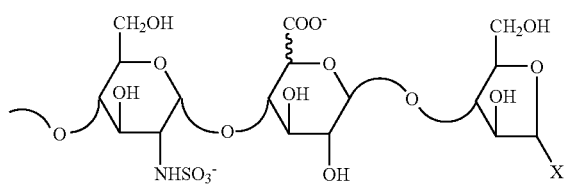
(b)

in which X is as defined above.

The presence of the structure (a) does not have any influence on the chemical characteristics of the (epi)K5-N-sulfates and their derivatives since any sulfations would involve a possible introduction of one or two sulfate groups which would not significantly change however the sulfation degree of the O-sulfated derivatives. Besides, the presence of the structure (a) does not influence biological activity of the products, as demonstrated by Østergaard et al. in Thrombosis Research, 1987, 45, 739-749 ("Østergaard 1987") for heparins of low molecular weight.

Particularly advantageous LMW-(epi)K5-N-sulfates according to the present invention are consisting of chain mixtures in which the preponderant species is a compound of formula I'b

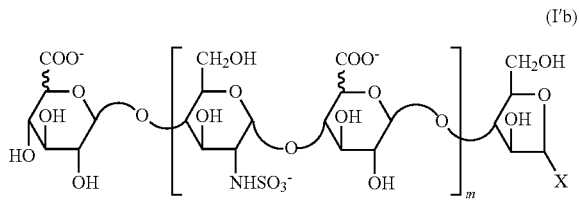
(I'b)

in which X is formyl or hydroxymethyl, m is 4, 5 or 6, the corresponding cation is one chemically or pharmaceutically acceptable ion, the uronic units are all of glucuronic acid or the glucuronic and iduronic units are present alternately, starting with a glucuronic or iduronic unit. In such case the Glucuronic/iduronic ratio is from 45/55 to 55/45, i.e., approximately 50/50.

All the LMW-(epi)K5-N-sulfates herein shown above are new products which constitute an additional object of the present invention.

The LMW-(epi)K5-N-sulfates, i.e., the LMW-K5-N-sulfates shown above and, unlike other epiK5-N-sulfates, for example as indicated in WO 92/17507, also the LMW-epiK5-N-sulfates of the present invention, being virtually free of N-acetyl groups, do not have anticoagulant activity and have an interesting activity against the free radicals. Thanks to their low toxicity, the new LMW-K5-N-sulfates and LMW-epiK5-N-sulfates are active ingredients for the preparation of pharmaceutical compositions utilizable as adjuvants in the treatment of ischemic cardiopathy and for the treatment of radiation dermatitis or of cosmetic compositions useful as anti-ageing of the skin.

When the LMW-(epi)K5-N-sulfates shown above are used as starting materials for the O-oversulfation reaction, it is in any case preferred that, in their preparation by nitrous depolymerization as shown above, said depolymerization is followed by the reduction for example with sodium borohydride to give LMW-K5-N-sulfates characterized by terminal units (a) in which X is hydroxymethyl, since according to the process of the present invention said LMW-(epi)K5-N-sulfates are subjected to reactions of sulfation and acylation whose influence, of the 2,5-anhydromannose radical of structure (a) is unknown on the formyl group, in which X represents formyl.

Said starting materials are preferably used in sodium salt form, unless a tertiary or quaternary organic base salt thereof prepared according to step (a) shown above, preferably the tetrabutylammonium salt, is already available.

According to the present invention, the starting (epi)-K5-N-sulfate-derivatives, preferably 100% N-sulfated, are subjected to the aforesaid steps (a) and (b), upon termination of which the corresponding, new (epi)K5-amine-O-oversulfate-derivatives are isolated, in which the amine is non-substituted, normally in sodium salt from, which can be transformed into another chemically or pharmaceutically acceptable salt.

Thus, according to another of its aspects, the present invention refers to new (epi)K5-amine-O-oversulfate-derivatives and their chemically or pharmaceutically acceptable salts, obtainable by a process characterized in that (a) an (epi)K5-N-sulfate-derivative, in acidic form, is treated with a tertiary or quaternary organic base, letting the reaction mixture to stand for a time period of 30-60 minutes, maintaining the pH of the solution at a value of approximately 7 by addition of said tertiary or quaternary organic base and its salt is isolated with said organic base; and (b) said salt of organic base of said (epi)K5-N-sulfate-derivative is treated with an O-sulfation reagent in the conditions of O-oversulfation- and the (epi)K5-amine-O-oversulfate-derivative is isolated.

The derivative thus obtained is generally an (epi)K(5-amine-O-oversulfate-derivative having a mean molecular weight from approximately 4,500 to approximately 40,000, isolated in sodium salt form which can be transformed into another chemically or pharmaceutically acceptable salt, Particularly advantageous salts are those of alkaline metals, alkaline-earth metals, of ammonium, tetra($C_1$-$C_4$)alkylammonium, aluminum and zinc and, among these, the salts of sodium, calcium and tetrabutylammonium are preferred.

As already herein shown above, the degree of sulfation of the (epi)K5-amine-O-oversulfate-derivatives as obtained above depends on the configuration of the starting (epi)K5-N-sulfate-derivative, since the steric bulk in the disaccharide chain of K5-N-sulfate-derivative, in which the uronic units are comprised exclusively of glucuronic acid, allows a oversulfation which is less than that occurring with the epiK5-N-sulfate-derivative, especially if the epimerization degree of the latter is 40-60% of glucuronic acid and 60-40% of iduronic acid.

In fact it has been ascertained that, subjecting a K5-N-sulfate-derivative to the aforesaid steps (a) and (b) a K5-amine-O-oversulfate-derivative is obtained having a sulfation degree from 2.2 to 3, advantageously from 2.5 to 3, preferably from 2.7 to 2.9.

Subjecting an epiK5-N-sulfate-derivative to the aforesaid steps (a) and (b) in which the iduronic acid content is 20-60%, preferably 40-60% of the total of the uronic acids, an epiK5-amine-O-oversulfate-derivative is obtained having a sulfation degree of at least 3.4, advantageously of at least 3.5, more advantageously from 3.55 to 4, preferably from 3.55 to 3.8.

These (epi)K5-amine-O-oversulfated-derivatives are useful products as intermediates in the preparation of their N-($C_1$-$C_4$)acylated derivatives and as active ingredients basically free of activity on the coagulation parameters but having other interesting pharmacobiological properties, useful for the preparation of pharmaceutical compositions.

For use of the epiK5-amine-O-oversulfate-derivatives of the present invention as active ingredients of pharmaceutical compositions, it is advantageous to prepare both derivatives of low molecular weight, with a mean molecular weight of from approximately 3,000 to approximately 11,500, preferably from approximately 4,500 to approximately 8,500, with a molecular weight distribution of between approximately 1,000 and approximately 15,000, preferably between approximately 2,000 and approximately 10,000 and derivatives of high molecular weight, originating from the unfractionated K5 polysaccharide, with a mean molecular weight of from approximately 15,000 to approximately 45,000, preferably between approximately 20,000 and approximately 45,000, with a molecular weight distribution from approximately 2,000 to approximately 70,000.

Thus, according to another of its aspects the invention provides new active ingredients of pharmaceutical compositions consisting of (epi)K5-amine-O-oversulfate-derivatives consisting of chain mixtures in which at least 90% of said chains have the formula II

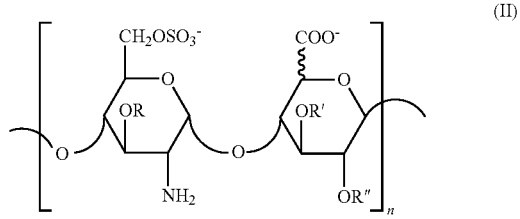

(II)

in which n is an integer from 2 to 100, preferably from 3 to 100, R, R' and R" are hydrogen or $SO_3^-$, the uronic units are all of glucuronic acid, for a sulfation degree of at least 2.2, advantageously from 2.2 to 3 or from 2.3 to 3, more advantageously from 2.5 to 3, preferably from 2.7 to 2.9, or are 20-60% consisting of iduronic acid, for a sulfation degree of at least 3.4, advantageously of at least 3.5, more advantageously from 3.55 to 4, preferably from 3.55 to 3.8 and the corresponding cation is chemically or pharmaceutically acceptable.

Advantageous epiK5-amine-O-oversulfated-derivatives of extremely high degree of sulfation are consisting of a chain mixture in which at least 90% of said chains have the formula II in which the uronic units are 40-60% consisting of iduronic acid, n is an integer from 2 to 100, preferably from 3 to 100, with a mean molecular weight of from approximately 2,000 to approximately 40,000, advantageously from approximately 4,500 to approximately 40,000, R is at least 40%, preferably 50-80% $SO_3^-$, R' and R" are both $SO_3^-$ or one is hydrogen and the other is 5-10% $SO_3^-$ in monosulfate glucuronic acid and 10-15% $SO_3^-$ in monosulfate iduronic acid, the degree of sulfation is more than 3.4 and the corresponding cation is chemically or pharmaceutically acceptable.

Preferred epiK5-amine-O-oversulfate-derivatives of very high degree of sulfation are the LMW-epiK5-amine-O-oversulfates consisting of a chain mixture in which at least 90% of said chains have the formula II'

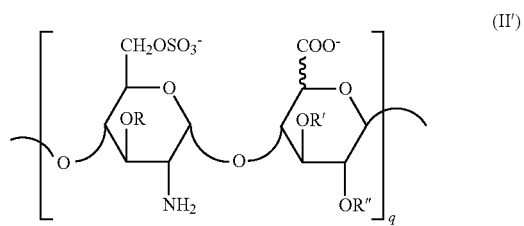

(II')

in which q is an integer from 2 to 20, X, R' and R" are hydrogen or $SO_3^-$, the uronic units are 20-60% comprised, preferably 40-60%, of iduronic acid, for a degree of sulfation from 3.55 to 4, and the corresponding cation is one chemically or pharmaceutically acceptable ion.

Mixtures of chain of formula I' in which 40-60%, preferably 50-55%, of the uronic units are those of iduronic acid, R is at least 40%, advantageously 50-80%, preferably approximately 65% $SO_3^-$, R' and R" are both $SO_3^-$ or one is hydrogen and the other is 5-10% $SO_3^-$ in glucuronic acid and 10-15% $SO_3^-$ in iduronic acid, n is an integer from 3 to 15, with a mean molecular weight from approximately 4,000 to approximately 8,000 and the corresponding cation is chemically or pharmaceutically acceptable are particularly interesting.

Among these LMW-epiK5-amine-O-oversulfates those consisting of a chain mixture in which the preponderant species has the formula II'a

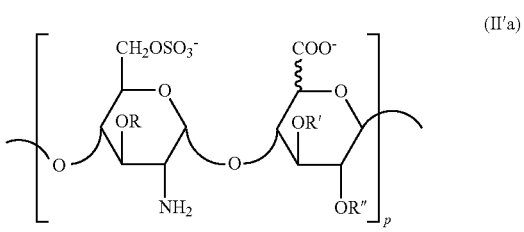

(II'a)

in which 40-60%, preferably 50-55%, of the uronic units are those of iduronic acid, p is an integer from 4 to 8, R, R' and R" are as defined above, the degree of sulfation is from 3.55 to 4 and the corresponding cation is chemically or pharmaceutically acceptable are preferred.

The origin of the new LMW-epiK5-amine-O-oversulfates from LMW-epiK5-N-sulfates obtained by nitrous depolymerization and subsequent reduction with, for example, sodium borohydride, involves, at the reducing end of the majority of the chains in said chain mixture, the presence of a sulfated 2,5-anhydromannitol unit of structure (a')

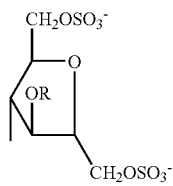

in which R represents hydrogen or $SO_3^-$.

Thus, the reducing end of the majority of the chains in said chain mixture is represented by the structure (b')

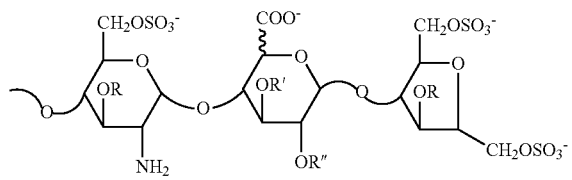

in which the uronic unit are all those of glucuronic acid or a 20-60% thereof are those of iduronic acid and the remaining ones those of glucuronic acid.

Among the aforesaid new LMW-epiK5-amine-O-oversulfates, those consisting of mixtures in which the preponderant species is a compound of formula II'b

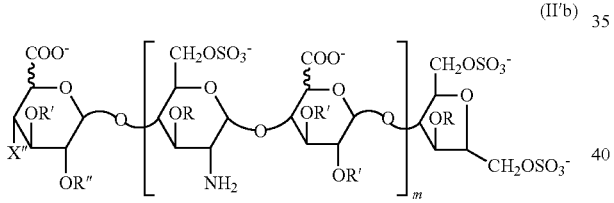

in which X, R' and R" are hydrogen or $SO_3^-$, X" is OH or $OSO_3^-$, m is 4, 5 or 6, the uronic units are 40-60% consisting of iduronic acid and the remaining ones being those of glucuronic acid, for a degree of sulfation from 3.55 to 4, the iduronic units being present alternately, starting with a glucuronic or iduronic unit, and the corresponding cation is one chemically or pharmaceutically acceptable ion, are preferred.

According to another of its aspects the invention provides new K5-amine-O-oversulfate-derivatives consisting of chain mixtures in which at least 90% of said chains have the formula III

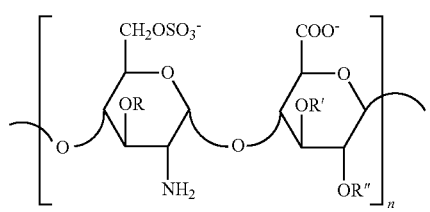

in which n is an integer from 2 to 100, preferably from 3 to 100, R, R' and R" are hydrogen or $SO_3^-$, the degree of sulfation is at least 2.2, advantageously from 2.2 to 3 or from 2.3 to 3, more advantageously from 2.5 to 3, preferably from 2.7 to 2.9 and the corresponding cation is chemically or pharmaceutically acceptable.

Preferred K5-amine-O-oversulfates are the LMW-K5-amine-O-oversulfates consisting of chain mixtures in which at least 90% of said chains have the formula III'

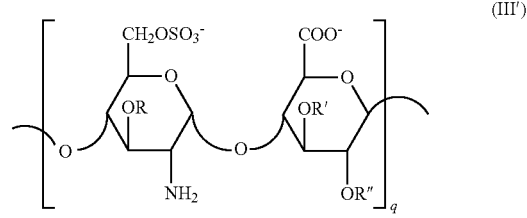

in which q is an integer from 2 to 20, X, R' and R" represent hydrogen or an $SO_3$ _ group, for a sulfation degree of at least 2.2, advantageously from 2.2 to 3 or from 2.3 to 3, more advantageously from 2.5 to 3, preferably from 2.7 to 2.9 and the corresponding cation is one chemically or pharmaceutically acceptable ion.

Among these LMW-K5-amine-O-oversulfates, those consisting of a chain mixture in which the preponderant species has the formula III'a

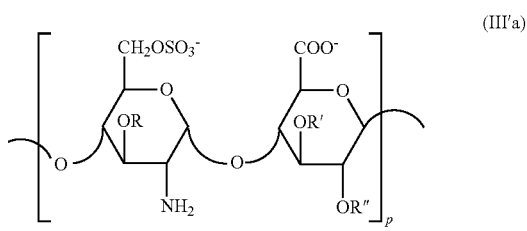

in which p is an integer from 4 to 8, R, R' and R" are as defined above, the degree of sulfation is at least 2.2, advantageously from 2.2 to 3 or from 2.3 to 3, more advantageously from 2.5 to 3, preferably from 2.7 to 2.9 and the corresponding cation is chemically or pharmaceutically acceptable, are preferred.

The origin of the new LMW-K5-amine-O-oversulfated from LMW-K5-sulfates obtained by nitrous depolymerization and subsequent reduction with, for example, sodium borohydride, involves, at the reducing end of the majority of the chains in said chain mixture, the presence of a sulfated 2,5-anhydromannitol unit of structure (a') as shown above, in which R represents hydrogen or $SO_3^-$.

Thus, the reducing end of the majority of the chains in said chain mixture is represented by the structure (b') as shown above, in which the uronic unit is that of glucuronic acid only.

Among the aforesaid new LMW-K5-amine-O-oversulfates, those consisting of mixtures in which the preponderant species is a compound of formula III'b

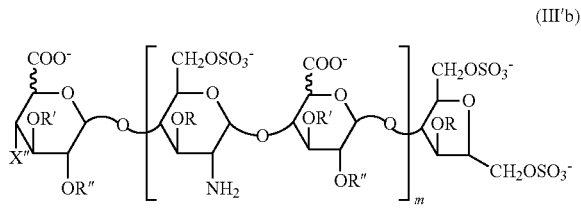

(III'b)

in which R, R' and R" are hydrogen or $SO_3^-$, X" is OH or $OSO_3^-$, for a sulfation degree of at least 2.2, advantageously from 2.2 to 3 or from 2.3 to 3, more advantageously from 2.5 to 3, preferably from 2.7 to 2.9, m is 4, 5 or 6 and the corresponding cation is one chemically or pharmaceutically acceptable ion, are preferred.

These LMW-K5-amine-O-oversulfates are new products useful as intermediates in the preparation of their N-sulfated or N-acylated derivatives but themselves have interesting pharmacological properties, in particular as anti-free radicals and microbicides, in particular powerful antiviral agents and, as such, constitute new active ingredients of pharmaceutical compositions which constitute therefore an additional aspect of the present invention.

In particular, according to another of its aspects, the invention concerns the use of the aforesaid (epi)K5-amine-O-oversulfate-derivatives with a high degree of sulfation for the preparation of new N-substituted epiK5-amine-O-oversulfate-derivatives.

The N-acyl-(epi)K5-amine-O-oversulfate-derivatives according to the present invention are obtained by subjecting the (epi)K5-amine-O-oversulfate-derivatives to the step (c) of the process of the present invention.

Thus, according to one of its additional aspects, the present invention provides new N-acyl-(epi)K5-amine-O-oversulfate-derivatives obtainable by a process characterized in that (a) an (epi)K5-N-sulfate-derivative, in acidic form, is treated with a tertiary or quaternary organic base, letting the reaction mixture to stand for a time period of 30-60 minutes, maintaining the pH of the solution at a value of 7 by addition of said tertiary or quaternary organic base and its corresponding organic base salt is isolated;

(b) said organic base salt of said (epi)K5-N-sulfate-derivative is treated with an O-sulfation reagent in the conditions of O-oversulfation; and (c) the product thus obtained is treated with a functional derivative of a ($C_2$-$C_4$) carboxylic acid, the N-acyl-(epi)K5-amine-O-oversulfate-derivative thus obtained is isolated.

Generally the N-acyl-(epi)K5-amine-O-oversulfate-derivative is isolated in sodium salt form and optionally said sodium salt is transformed into another chemically or pharmaceutically acceptable salt.

As occurs for the (epi)K5-amine-O-oversulfate-derivatives, also the degree of sulfation of the N-acyl-(epi)K5-amine-O-oversulfate-derivatives as obtained above depends on the configuration of the starting (epi)K5-N-sulfate-derivative, since the steric bulk of the disaccharide chain of K5-N-sulfate-derivative, in which the uronic units are those of glucuronic acid only, allows an oversulfation which is less than that occurring with the epiK5-N-sulfate-derivative, especially if the epimerization degree of the latter is 40-60% of glucuronic acid and 60-40% of iduronic acid.

In fact, it has been ascertained that, by subjecting a K5-N-sulfate-derivative to the aforesaid steps (a)-(c) an N-acyl-K5-amine-O-oversulfate-derivative is obtained having a degree of sulfation from 2.2 to 3' advantageously from 2.5 to 3, preferably from 2.7 to 2.9.

Subjecting an epiK5-N-sulfate-derivative in which the iduronic acid content is 20-60% of the total of the uronic acids to the aforesaid steps (a), (b) and (c), N-acyl-epiK5-amine-O-oversulfate-derivatives are obtained having a sulfation degree of at least 3.4, advantageously of at least 3.5, more advantageously from 3.55 to 4, preferably from 3.55 to 3.8.

Thus, according to another of its aspects, the present invention provides new N-acyl-(epi)K5-amine-O-oversulfate-derivatives, in which the acyl is that of a ($C_2$-$C_4$) carboxylic acid, having a mean molecular weight from approximately 2,000 to approximately 45,000, preferably between approximately 4,500 and approximately 40,000, a degree of sulfation as indicated above, said derivatives being basically inactive on the coagulation parameters but useful active ingredients of pharmaceutical or cosmetic compositions.

For use of the N-acyl-epiK5-amine-O-oversulfate-derivatives of the present invention as pharmaceutical or cosmetic products it is advantageous to prepare both derivatives of low molecular weight, with a mean molecular weight from approximately 3,000 to approximately 11,500, preferably from approximately 4,500 to approximately 8,500, with a molecular weight distribution of between approximately 1,000 and approximately 15,000, preferably between approximately 2,000 and approximately 10,000 and derivatives of high molecular weight, originating from the unfractionated K5, with a mean molecular weight from approximately 15,000 to approximately 45,000, preferably between approximately 20,000 and approximately 45,000, with a molecular weight distribution from approximately 2,000 to approximately 70,000.

In the N-acyl-epiK5-amine-O-oversulfate-derivatives of the present invention, the degree of sulfation is very high since, in respect of the 4 free hydroxyls available per disaccharide unit, at least 3.4, preferably from 3.5 to 3.8, are sulfated, whereas the nitrogen of the glucosamine is virtually 100% acylated. Besides, the N-acyl-epiK5-amine-O-oversulfate-derivatives are 100% 6-O-sulfated and 50-80% 3-O-sulfated in their glucosamine units, 5-10% 3-O-monosulfated in glucuronic units, 10-15% O-monosulfated in iduronic units and 2.3-di-O-sulfated in the remaining uronic units, considering that the degree of sulfation is at least 3.4.

The N-acyl-K5-amine-O-oversulfate-derivatives which, as indicated above, have a degree of sulfation from 2.2 to 3, are at least 90% 6-O-sulfated.

According to another of its aspects, the invention provides new N-acyl-epiK5-amine-O-oversulfate-derivatives consisting of chain mixtures in which at least 90% of said chains have the formula IV

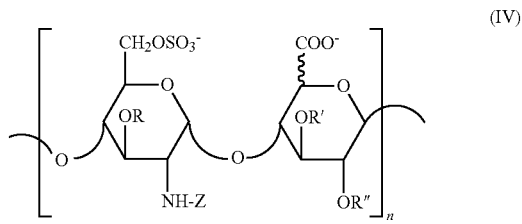

(IV)

in which the uronic units are 20-60% consisting of iduronic acid, the remaining ones being those of glucuronic acid, n is an integer from 2 to 100, preferably from 3 to 100, R, R' and R" are hydrogen or $SO_3^-$, Z is ($C_2$-$C_4$)acyl, the degree of sulfation is at least 3.4, advantageously of at least 3.5, more advantageously from 3.55 to 4, preferably from 3.55 to 3.8 and the corresponding cation is chemically or pharmaceutically acceptable.

Advantageous N-acyl-epiK5-amine-O-oversulfate-derivatives of extremely high degree of sulfation are those consisting of a mixture of chains in which at least 90% of said chains have the formula IV in which the uronic units are 40-60% consisting of iduronic acid, the remaining ones being those of glucuronic acid, n is an integer from 2 to 100, preferably from 3 to 100, with a mean molecular weight from approximately 2,000 to approximately 45,000, advantageously from approximately 4,500 to approximately 45,000, R is at least 40%, preferably 50-80% $SO_3^-$, R' and R" are both $SO_3^-$ or one is hydrogen and the other is 5-10% $SO_3^-$ in monosulfate glucuronic acid and 10-15% $SO_3^-$ in monosulfate iduronic acid, the degree of sulfation is more than 3.4 and the corresponding cation is chemically or pharmaceutically acceptable.

The N-acyl-epiK5-amine-O-oversulfate-derivatives of extremely high degree of sulfation of particular interest are N-acyl-LMW-epiK5-amine-O-oversulfates consisting of a chain mixture in which at least 90% of said chains have the formula IV'

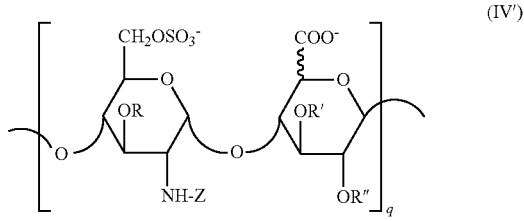

(IV')

in which q is an integer from 2 to 20, R, R' and R" represent hydrogen or an $SO_3^-$ group for a degree of sulfation from 3.55 to 4, Z is $(C_2-C_4)$acyl, and the corresponding cation is one chemically or pharmaceutically acceptable ion.

Chain mixtures of formula IV' in which the uronic units consist of 40-60%, preferably 50-55%, of iduronic acid, the remaining ones being those of glucuronic acid, R is at least 40%, advantageously 50-80%, preferably approximately 65% $SO_3^-$, R' and R" are both $SO_3^-$ or one is hydrogen and the other is 5-10% $SO_3^-$ in glucuronic acid and 10-15% $SO_3^-$ in iduronic acid, q is an integer from 3 to 15, with a mean molecular weight from approximately 4,500 to approximately 9,000 and the corresponding cation is chemically or pharmaceutically acceptable are preferred.

Other particularly interesting N-acyl-LMW-epiK5-amine-O-oversulfates are those of very low molecular weight, consisting of a chain mixture in which the preponderant species is a compound of formula IV'a

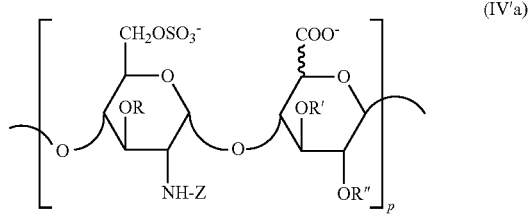

(IV'a)

in which p is an integer from 4 to 8, R', R' and R" are hydrogen or an $SO_3^-$ group for a degree of sulfation from 3.55 to 4, Z is $(C_2-C_4)$acyl, and the corresponding cation is one chemically or pharmaceutically acceptable ion.

The origin of the new N-acyl-LMW-epiK5-amine-O-oversulfates from LMW-epiK5-sulfates obtained by nitrous depolymerization and subsequent reduction with, for example, sodium borohydride, involves, at the reducing end of the majority of the chains in said chain mixture, the presence of a sulfated 2,5-anhydromannitol unit of structure (a') defined above, in which R represents hydrogen or $SO_3^-$.

Thus, the reducing end of the majority of the chains in said chain mixture is represented by the structure (b")

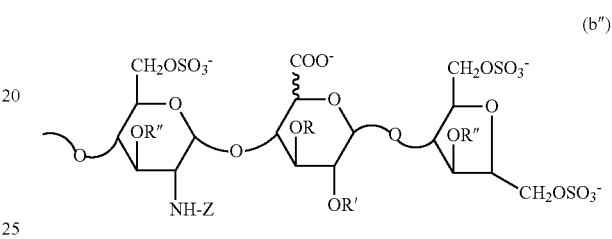

(b")

in which Z represents $(C_2-C_4)$acyl and the uronic unit can be glucuronic or iduronic, Among the aforesaid new N-acyl-LMW-epiK5-amine-O-oversulfates, those consisting of mixtures in which the preponderant species is a compound of formula IV'b

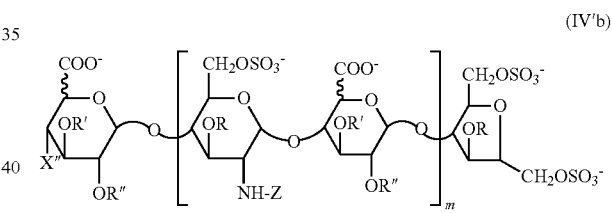

(IV'b)

in which R, R' and R" are hydrogen or $SO_3^-$, Z is $(C_2-C_4)$acyl, X" is OH or $OSO_3^-$, m is 4, 5 or 6, for a degree of sulfation from 3.55 to 4, the uronic units are present alternately, starting with a glucuronic or iduronic unit, and the corresponding cation is one chemically or pharmaceutically acceptable ion are preferred.

Said cations are advantageously those of alkaline metals, alkaline-earth metals, of ammonium, tetra($C_1$-$C_4$)alkylammonium, aluminum and zinc and, among these, preferably the salts of sodium, calcium and tetrabutylammonium.

In all the N-acyl-epiK5-amine-O-oversulfates shown above, in particular those of formula IV, IV', IV'a, IV'b, as also in the structure b", the acyl group (Z) is preferably a ($C_2$-$C_4$) acyl selected among the group consisting of acetyl, (2-carboxy)acetyl, (2-methoxycarbonyl)acetyl, (2-ethoxycarbonyl)acetyl, propionyl, (3-carboxy)propionyl, N-(3-methoxycarbonyl)propionyl and (3-ethoxycarbonyl)propionyl.

According to another of its aspects, the invention provides new N-acyl-K5-amine-O-oversulfate-derivatives consisting of chain mixtures in which at least 90% of said chains have the formula V

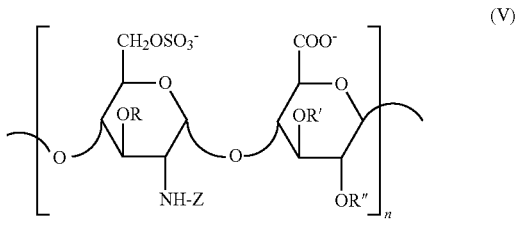
(V)

in which n is an integer from 2 to 100, preferably from 3 to 100, Z is (C$_2$-C$_4$)acyl, R, R' and R" are hydrogen or SO$_3^-$, the degree of sulfation is at least 2.2, advantageously from 2.2 to 3 or from 2.3 to 3, more advantageously from 2.5 to 3, preferably from 2.7 to 2.9 and the corresponding cation is chemically or pharmaceutically acceptable.

Particularly interesting are new N-acyl-LMW-K5-amine-O-oversulfates consisting of chain mixtures in which at least 90% of said chains have the formula V'

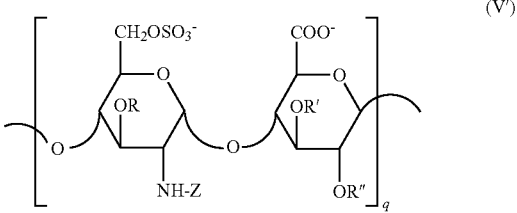
(V')

in which q is an integer from 2 to 20, Z is (C$_2$-C$_4$)acyl, R, R' and R" represent hydrogen or an SO$_3^-$ group for a sulfation degree of at least 2.2, advantageously from 2.2 to 3 or from 2.3 to 3, more advantageously from 2.5 to 3, preferably from 2.7 to 2.9 and the corresponding cation is one chemically or pharmaceutically acceptable ion.

Among these N-acyl-LMW-K5-amine-O-oversulfates, those consisting of a chain mixture in which the preponderant species has the formula V'a

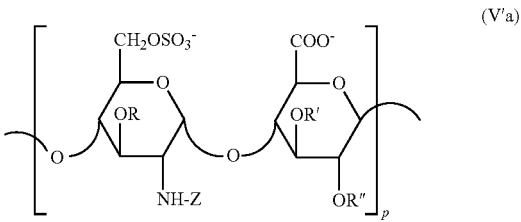
(V'a)

in which p is an integer from 4 to 8, Z is (C$_2$-C$_4$)acyl, R, R' and R" are as defined above, the degree of sulfation is at least 2.2, advantageously from 2.2 to 3 or from 2.3 to 3, more advantageously from 2.5 to 3, preferably from 2.7 to 2.9 and the corresponding cation is chemically or pharmaceutically acceptable are preferred.

The origin of the new N-acyl-LMW-K5-amine-O-oversulfates from LMW-K5-sulfates obtained by nitrous depolymerization and subsequent reduction with, for example, sodium borohydride, involves, at the reducing end of the majority of the chains in said chain mixture, the presence of a sulfated 2,5-anhydromannitol unit of structure (a') as shown above, in which R represents hydrogen or SO$_3^-$.

Thus, the reducing end of the majority of the chains in said chain mixture is represented by the structure (b''')

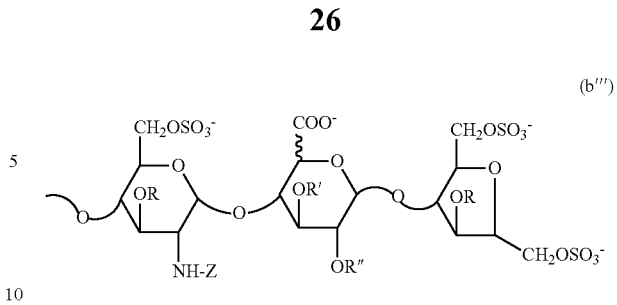
(b''')

in which Z, R, R' and R" are as defined above.

Among the aforesaid new N-acyl-LMW-K5-amine-O-oversulfates, those consisting of mixtures in which the preponderant species is a compound of formula V'b

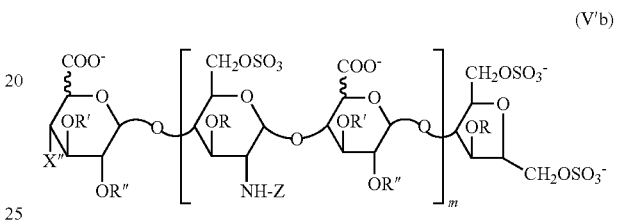
(V'b)

in which Z is (C$_2$-C$_4$)acyl, R, R' and R" are hydrogen or SO$_3^-$, X" is OH or OSO$_3^-$, for a sulfation degree of at least 2.2, advantageously from 2.2 to 3 or from 2.3 to 3, more advantageously from 2.5 to 3, preferably from 2.7 to 2.9, m is 4, 5 or 6 and the corresponding cation is one chemically or pharmaceutically acceptable ion are preferred.

In all the N-acyl-K5-amine-O-oversulfates shown above, in particular those of formula V, V', V'a, V'b, as also in the structure b''', the acyl group (Z) is preferably a (C$_2$-C$_4$)acyl selected among the group consisting of acetyl, (2-carboxy)acetyl, (2-methoxycarbonyl)acetyl, (2-ethoxycarbonyl)acetyl, propionyl, (3-carboxy)propionyl, N-(3-methoxycarbonyl)proponyl and (3-ethoxycarbonyl)proponyl.

Particularly interesting are the N-acyl-K5-amine-O-oversulfates shown above in which Z is a (C$_2$-C$_4$)acyl different from acetyl. Also interesting and particularly active are the N-acyl-K5-amine-O-oversulfates shown above, in which Z is acetyl, having a degree of sulfation of 2.7-2.9, preferably of approximately 2.8.

The new N-acyl-(epi)K5-amine-O-oversulfate-derivatives, especially in their salts form, are highly anionic products able to capture the free radicals. These can be used in the cosmetics industry as coadjuvants against hair loss or to prepare "anti-ageinig" creams, but are above all useful in the pharmaceutical industry, as products for the treatment of dermatitis and as microbicides.

Thus, according to one of its additional aspects, the present invention provides pharmaceutical compositions including, as one of their active ingredients, a pharmacologically active amount of an N-acyl-(epi)K5-amine-O-oversulfate-derivative as shown above or of one of its pharmaceutically acceptable salts, in admixture with a pharmaceutical carrier.

The dose regimen can vary widely depending on the age, the weight and health condition of the patient. This dose regimen includes the administration of a dose from 1 to 1000 mg, advantageously from 10 to 750 mg, preferably 250 to 500 mg from one to three times a day by intravenous, subcutaneous, oral, transdermal or topical administration.

The present invention also provides a cosmetic composition including an effective amount of an N-acyl-(epi)K5- amine-O-oversulfate-derivative or one of its pharmaceutically acceptable salts, in mixture with a cosmetic excipient.

Besides, as illustrated hereinabove, all the (epi)K5-amine-O-oversulfate-derivatives having a sulfation degree of from 2 to 4 have microbicidal activity and are active ingredients of pharmaceutical compositions for the treatment of infectious, in particular viral, diseases. Advantageously, said pharmaceutical compositions comprise, as an active ingredient thereof a pharmacologically effective amount of an (epi)K5-amine-O-oversulfate-derivative, having a sulfation degree of from 2 to 4, obtainable by treating a tertiary or quaternary organic base salt of an (epi)K5-N-sulfate with a sulfation agent under O-oversulfation conditions, or a pharmaceutically acceptable salt thereof in admixture with a pharmaceutical carrier.

In particular, according to another of its aspects, the invention provides a pharmaceutical composition comprising, as active ingredient, a pharmacologically active amount of an (epi)K5-amine-O-oversulfate-derivative having a sulfation degree of from 2 to 4, or of a pharmaceutically acceptable salt thereof obtainable by treating a tertiary or quaternary organic base salt of an (epi)K5-N-sulfate-derivative with a O-sulfating agent under O-oversulfation conditions, said (epi)K5-N-sulfate-derivative salt with said organic base having been isolated according to known methods, in particular by lyophilization, immediately after its formation at a pH of from about 5 to about 9, in admixture with a pharmaceutical carrier.

More precisely, the (epi)K5-amine-O-oversulfate-derivative used as active ingredient of the compositions of the present invention is obtainable by (a1') treating an (epi)K5-N-sulfate-derivative, in its acidic form, with a tertiary or quaternary organic base and isolating its salt with said tertiary or quaternary organic base immediately after its formation, at a pH of from about 5 to about 9; and (a2') treating said tertiary or quaternary organic base salt of said (epi)K5-N-sulfate-derivative with an O-sulfation agent under the conditions of an O-oversulfation and isolating the (epi)K5-amine-O-oversulfate-derivative as the sodium salt thereof which can subsequently be converted into another salt.

More particularly, the present invention provides a pharmaceutical composition including, as one of its active ingredients, an (epi)K5-amine-O-oversulfate-derivative obtainable according to steps (a) and (b) of the process described above, or one of its pharmaceutically acceptable salts, in mixture with a pharmaceutical excipient. Advantageously, said (epi)K5-amine-O-oversulfate-derivative is consisting of a chain mixture in which at least 90% of said chains have the formula II, II', III or III' or in which the preponderant species is a compound of formula IIa, II'a, III'a or III'b. Preferred active ingredient is a LMW-K5-amine-O-oversulfate having a degree of sulfation from 2.2 to 3, advantageously having a mean molecular weight from approximately 3,500 to approximately 11,000, more advantageously from approximately 3,500 to approximately 5,200 and practically free of N-acetyl and N-sulfate groups.

In the pharmaceutical compositions of the present invention for oral, subcutaneous, intravenous, transdermal, ophthalmic or topical administration, the active ingredients (epi) K5-amine-O-oversulfate-derivatives are preferably administered in the form of dosage units, in mixture with the classic pharmaceutical excipients or vehicles. The dose regimen can vary widely depending on the age, the weight and health condition of the patient. This dose regimen includes the administration of a dose of an (epi)K5-amine-O-oversulfate-derivative from 1 to 1000 mg, advantageously from 10 to 750 mg, preferably 250 to 500 mg from one to three times a day by intravenous, subcutaneous, oral, transdermal, ophthalmic or topical administration.

The pharmaceutical compositions comprising an (epi)K5-amine-O-oversulfate-derivative such as those shown above are formulated with the classic carriers suitable for the different ways of administration.

Particularly advantageous are the formulations in the form of creams, ointments, liniments, gels, foams, balsams, vaginal pessaries, suppositories, solutions or suspensions suitable for local administration.

Finally, the present invention provides a pharmaceutical composition containing, as one of its active ingredients, a pharmacologically active amount of a LMW-(epi)K5-N-sulfate, i.e., of a LMW-K5-N-sulfate or of a LMW-epiK5-N-sulfate as shown above or of one of their pharmaceutically acceptable salts, in mixture with a pharmaceutical excipient.

In the pharmaceutical compositions of the present invention for oral, subcutaneous, intravenous, transdermal or topical administration, the LMW-(epi)K5-N-sulfate active ingredients are preferably administered in the form of dosage units, in mixture with the classic pharmaceutical excipients or vehicles.

The dose regimen can vary widely depending on the age, the weight and health condition of the patient. This dose regimen includes the administration of a dose from 1 to 1000 mg, advantageously from 10 to 750 mg, preferably 250 to 500 mg from one to three times a day by intravenous, subcutaneous, oral, transdermal or topical administration. These dosage unit forms may contain any of the above products, in particular any N-acyl-(epi)K5-amine-O-oversulfate-derivative or any (epi)K5-amine-O-oversulfate-derivative in the above amount ranges because they are practically non-toxic products.

According to another of its aspects, the present invention also provides a cosmetic composition containing, as one of its active ingredients, an effective amount of a LMW-K5-N-sulfate or LMW-epiK5-N-sulfate or of one of its pharmaceutically acceptable salts, in mixture with a cosmetic excipient.

Advantageously, said LMW-(epi)K5-N-sulfate-derivative is consisting of a chain mixture in which at least 90% of said chains have the formula I, or I', or in which the preponderant species is a compound of formula I'a, or I'b. Preferred active ingredient is a LMW-(epi)K5-N-sulfate-derivative having a mean molecular weight from approximately 1,000 to approximately 12,000, advantageously from approximately 1,500 to approximately 8,000, preferably from approximately 1,500 to approximately 7,500 and practically free of N-acetyl groups.

A salt selected from the group consisting of salts of alkaline metals or alkaline-earth metals, of ammonium, tetra($C_1$-$C_4$) alkylammonium, aluminum or zinc, in particular the salt of sodium, potassium, calcium, magnesium, aluminum or zinc constitutes an effective active ingredient of the compositions of the present invention.

The following examples illustrate the invention without however limiting it.

PREPARATION I

LMW-epiK5-N-sulfate a) Epimerization of K5-N-sulfate

Two g of K5 N-sulfate, obtained as described in Example 2, steps (i) and (ii), of WO 02/068477, are dissolved in 120 ml of 25 mM HEPES buffer, pH 7, containing 50 mM $CaCl_2$. The solution obtained is made to recirculate through a 50 ml column filled with the resin containing the immobilized enzyme obtained as described in WO 96/14425. This operation is carried out at 30° C. with a flow of 200 ml/h for 24 hours. The product obtained is purified by ultrafiltration over a 1000 D membrane and passage over an ionic exchange column IR 120 H$^+$, neutralizing the eluate with 1N NaOH. The sample is recovered by precipitation with ethanol or acetone. An epimerized product is obtained with an iduronic acid/glucuronic acid ratio of 55/45 against a ratio of 0/100 of the starting product. The percentage of epimerization was calculated with $^1$H-NMR according to the method described in WO 96/14425. The yield, calculated by measuring the content of uronic acids against a standard with the carbazole method (Bitter and Muir, Anal. Biochem., 1971, 39, 88-92) is 90%.

b) Depolymerization of epi-K5-N-sulfate

One g of product obtained in step (a) is depolymerized by the degradation method with nitrous acid and subsequent reduction of the aldehyde which forms. In particular one continues by dissolving the product in 25 ml of distilled water and adding it with 230 mg of sodium nitrite dissolved in 115 ml of distilled water. The solution is then brought to 4° C. and the pH to 2 with 0.1 N HCl and maintained for 30 minutes. At the end of the reaction the solution is brought to room temperature and the pH to 7 with 0.1 M NaOH. The solution is then added with 450 mg of NaBH$_4$ and reacted for 4 hours. The product is recovered by precipitation with 3 volumes of acetone at 4° C., filtration with filtering funnel and dried at 40° C. in a vacuum oven. 900 mg of LMW-epiK5-N-sulfate with a molecular weight distribution measured with HPLC method which ranges from 1,000 to 4,000 and with a glucuronic unit content of 45% and iduronic unit content of 55% are obtained,

PREPARATION II

LMW-K5-N-sulfate

The product obtained as described in Example 2, steps (i) and (ii), of WO 02/068477 is depolymerized by the degradation method with nitrous acid and subsequent reduction of the aldehyde which forms. One continues by dissolving 1 g of K5-N-sulfate in 200 ml of distilled water and adding it with 480 mg of sodium nitrite dissolved in 240 ml of distilled water. The solution is then brought to 4° C. and the pH to 2 with 0.1 N HCl and maintained for 30 minutes. At the end of the reaction the solution is brought to pH 7 with 0.1 M NaOH and then to room temperature. The solution is then added with 450 mg of NaBH$_4$ and reacted for 4 hours. The excess NaBH$_4$ is eliminated with HCl bringing the pH to 5-6. The product, neutralized with 0.1 M NaOH, is recovered by precipitation with 3 volumes of acetone at 4° C., filtration with filtering funnel and dried at 40° C. in a vacuum oven. 900 mg of LMW-K5-N-sulfate with a mean molecular weight of approximately 2,000, consisting of a chain mixture in which the preponderant species is a compound of formula I'b in which m is 4 and the uronic units are those of glucuronic acid are obtained.

PREPARATION III (a) Depolymerization of K5-N-sulfate

Two g of K5-N-sulfate obtained as described in Example 2, steps (i) and (ii), of WO 02/068477 is depolymerized as described in PREPARATION II, utilizing 100 mg of sodium nitrite and 300 mg of sodium borohydride. 1.8 g. of LMW-K5-N-sulfate with a mean molecular weight of 5,000 are obtained.

(b) Epimerization of LMW-K5-N-sulfate

One g of LMW-K5 N-sulfate obtained in step (a) is treated as described in step (a) of the Example 1. An epimerized product is obtained with an iduronic acid/glucuronic acid ratio of 44/56 against a ratio of 0/100 of the starting product, with a molecular weight distribution from 2,000 to 10,000 and with a mean molecular weight of 5,000 D. The yield, calculated by measuring the content of uronic acids against a standard with the carbazole method (Bitter and Muir Anal. Biochem. 39, 88-92-1971) is 90%,

PREPARATION IV

Preparation of an epiK5-N-sulfate

A solution of 10 g of K5-N-sulfate obtained as described in Example 2, steps (i) and (ii), of WO 02/068477 in 600 ml of 25 mM HEPES buffer at pH 7, containing CaCl$_2$ at a concentration of 50 mM is made to recirculate through a 50 ml column filled with Sepharose 4B resin containing 5 g of recombinant C5-epimerase (WO 96/14425) immobilized as described in WO 01/72848. The reaction is carried out at 30° C. at pH 7 with a flow of 200 ml/h for 24 hours. The product obtained is purified by ultrafiltration and precipitation with ethanol. Thus an epiK5-N-sulfate is obtained whose iduronic acid content is 54%.

PREPARATION V

Preparation of a LMW-epiK5-N-sulfate

One g of product obtained in PREPARATION IV is depolymerized by the degradation method with nitrous acid and subsequent reduction of the aldehyde which forms. In particular one continues by dissolving the product in 25 ml of distilled water and adding it with 230 mg of sodium nitrite dissolved in 115 ml of distilled water. The solution is then brought to 4° C. and the pH to 2 with 0.1 N HCl and maintained for 30 minutes. At the end of the reaction the solution is brought to room temperature and the pH to 7 with 0.1 M NaOH. The solution is then added with 450 mg of NaBH4 and reacted for 4 hours. The product is recovered by precipitation with 3 volumes of acetone at 4° C., filtration with filtering funnel and dried at 40° C. in a vacuum oven. 900 mg of LMW-epiK5-N-sulfate are obtained with a molecular weight distribution measured with HPLC method which ranges from 1,000 to 4,000.

PREPARATION VI

Depolymerized-LMW-epiK5-N-sulfate Having a Mean Molecular Weight of About 2,000

To a solution of 1 g of epiK5-N-sulfate, obtained as described in Example 12, paragraphs [0251]-[0265] of US 2002/0062019, in 200 ml of distilled water, 480 mg of sodium nitrite dissolved in 240 ml of distilled water are added. The solution is then brought to 4° C., the pH is adjusted to 2 with 0.1 N HCl and maintained for 30 minutes. At the end of the reaction the solution is brought to pH 7 with 0.1 M NaOH and then to room temperature. The solution is then added with 450 mg of NaBH$_4$ and reacted for 4 hours. The excess NaBH$_4$ is eliminated by adjusting the pH to 5-6 with HCl. The product, neutralized with 0.1 M NaOH, is recovered by precipitation with 3 volumes of acetone at 4° C., filtration with filtering funnel and dried at 40° C. in a vacuum oven. 900 mg of depolymerized-LMW-epiK5-N-sulfate are obtained with a mean molecular weight of approximately 2,000, consisting of a mixture of chains in which the preponderant species is a compound of formula I'b in which m is 4.

PREPARATION VII

Depolymerized-LMW-epiK5-N-sulfate with Mean Molecular Weight of 6,000 Starting K5-N-sulfate A solution of 8 g of 95% pure K5 polysaccharide in 800 ml of 2N NaOH is heated to 60° C. for 24 hours. After cooling, the solution is brought to pH 7 by 6N HCl. To the thus neutralized solution, at first 12.8 g of sodium carbonate, then, portionwise in 4 hours, 12.8 g of pyridine.$SO_3$ adduct in solid form are added. The reaction mixture is kept at 40° C. for 24 hours. After elimination of the salts by ultrafiltration on membrane Millipore Prepscale TFF 1000 D cut-off, the obtained product is recovered by precipitation with 3 volumes of acetone. Thus, 8 g of K5-N-sulfate are obtained. Its $^1$H-NMR spectrum shows a 100% N-sulfation (absence of signals due to $NH_2$ and acetyl groups).

Depolymerized-LMW-epi-K5-N-sulfate. Sequence (i)→(ii)

(i) Epimerization. The 8 g of K5 N-sulfate thus obtained are dissolved in 200 ml di Hepes 0.25M pH 7 buffer containing 50 mM $CaCl_2$ and treated in solution with $9.6 \times 10^{10}$ cpm of recombinant C5-epimerase at 30° C. for 24 hours at pH 7. At the end of the reaction, the sample is purified by elimination of the salts by ultrafiltration on Millipore Prepscale TFF 1000 D cut-off membrane and, then, precipitated with 3 volumes of acetone. Thus, 7.5 g of epiK5-N-sulfate are obtained. Its epimerization percentage, in practice the amount of iduronic units in respect of the glucuronic ones, calculated by $^1$H-NMR according to the method described in WO 96/4425, is 52%.

Figure 8:
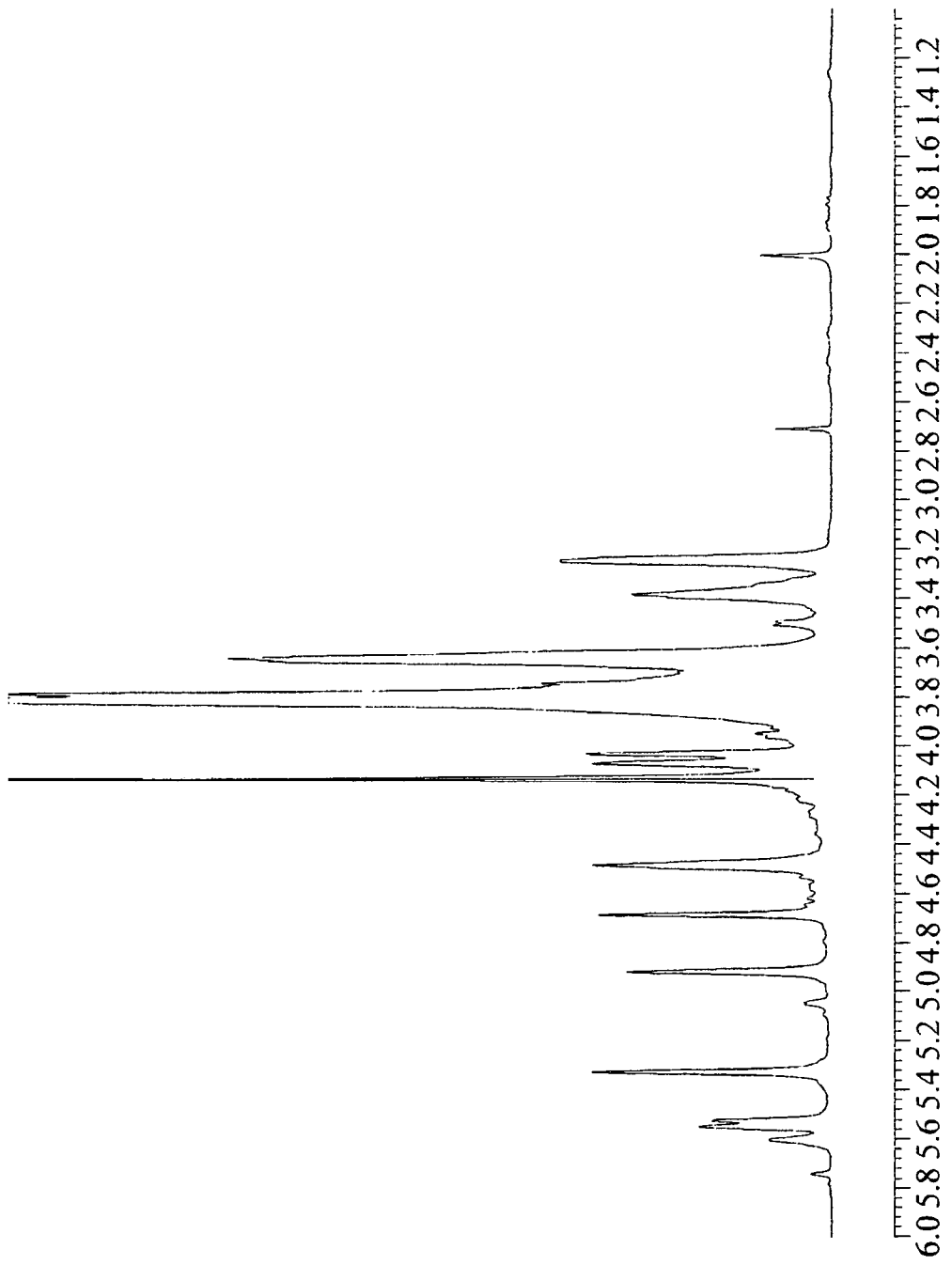
FIG. 8 shows the $^1$H-NMR spectrum of the depolymerized-LMW-epiK5-N-sulfate with mean molecular weight of 6,000 of PREPARATION VII.
Figure 9:
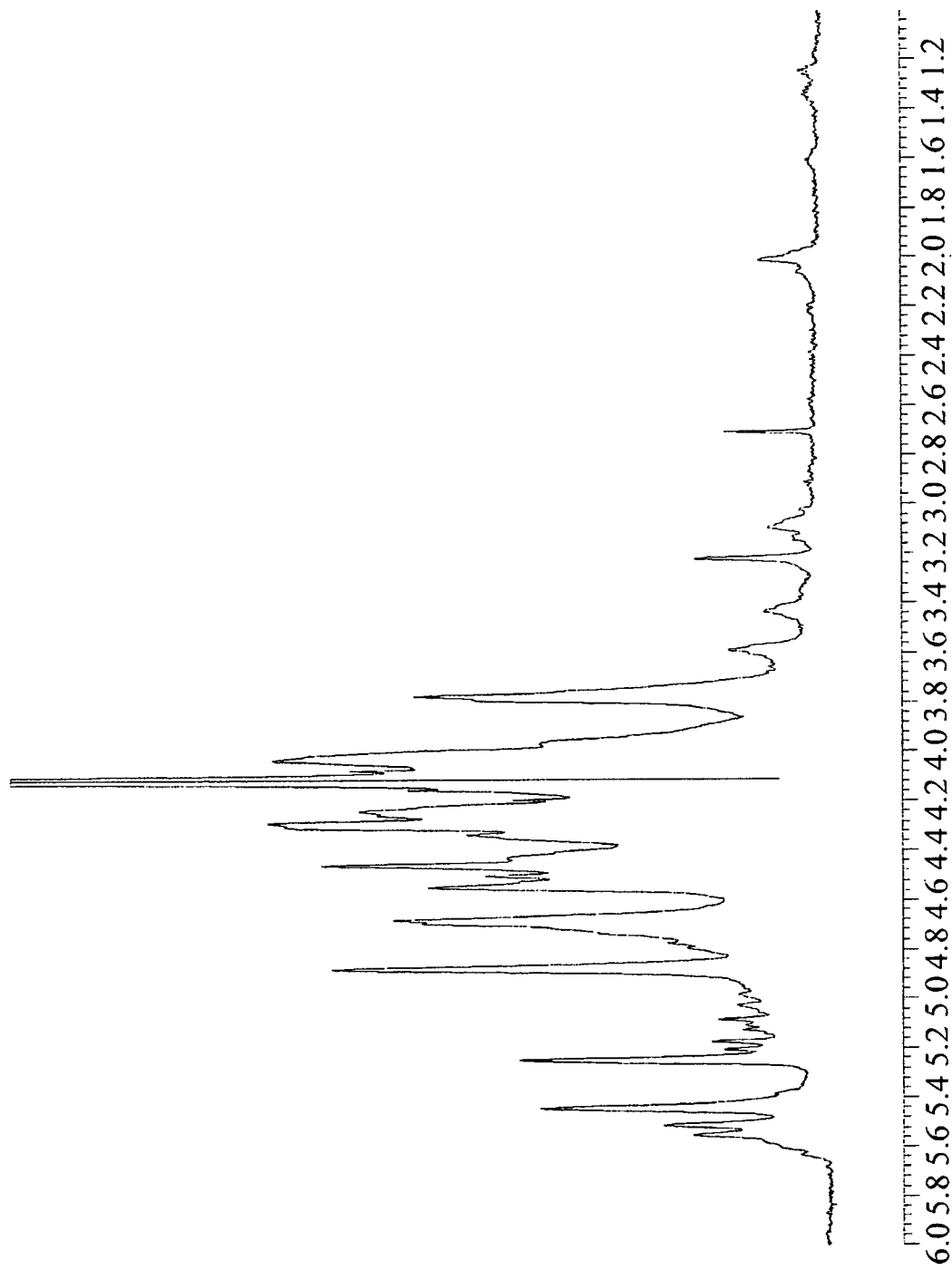
FIG. 9 shows the $^1$H-NMR spectrum of the depolymerized-LMW-epiK5-amine-O-oversulfate with mean molecular weight of 6,000 of Example 4(b).

(ii) Depolymerization. The 7.5 g of epiK5-N-sulfate thus obtained are dissolved in 150 ml water and the solution is thermostated at 4° C., then the pH is brought to 2.2 by previously cooled 1M HCl. To the solution, 431.2 mg of sodium nitrite, corresponding to 21.56 ml of a 2% solution of sodium nitrite in water, are added. The pH is brought to 2.2 again and the reaction mixture is kept at 4° C. for 20 minutes under stirring. After neutralization to pH 7.0 with 6N HCl, 1.35 g of sodium borohydride are added to the solution. The reduction is carried out by keeping the reaction mixture at room temperature for 4 hours, then the excess of reducing agent is destroyed by bringing the pH to 5 with 1N HCl, stirring until disappearance of effervescence. The pH is brought to 7-7.2 again with 1 M NaOH. The depolymerized product is recovered by ultrafiltration with Millipore TFF 1000 D cut-off membrane and subsequent precipitation with 3 volumes of acetone. Thus, 7 g of depolymerized-LMW-K5-N-sulfate are obtained. The mean molecular weight of this product, calculated via HPLC, is 6,000 D. Its $^1$H-NMR spectrum is shown in FIG. 8.

EXAMPLE 1

EpiK5-amine-O-oversulfate (a) Tetrabutylammonium salt of epiK5-N-sulfate

A solution of 400 mg of epiK5-N-sulfate with an iduronic acid content of 54% as obtained in PREPARATION TV in 40 ml of water is thermostated at 4° C., then passed over an ionic exchange resin IR 120 $H^+$ preconditioned with water at 4° C. The eluate obtained, consisting of 100 ml of a solution at pH 1.94, is neutralized with a solution of 15% tetrabutylammonium hydroxide and left at room temperature for one hour, maintaining the pH at 7 by addition of 15% tetrabutylammonium hydroxide and finally is lyophilized. Thus 805 mg of tetrabutylammonium salt of epiK5-N-sulfate are obtained.

(b) EpiK5-amine-O-oversulfate

Figure 7:
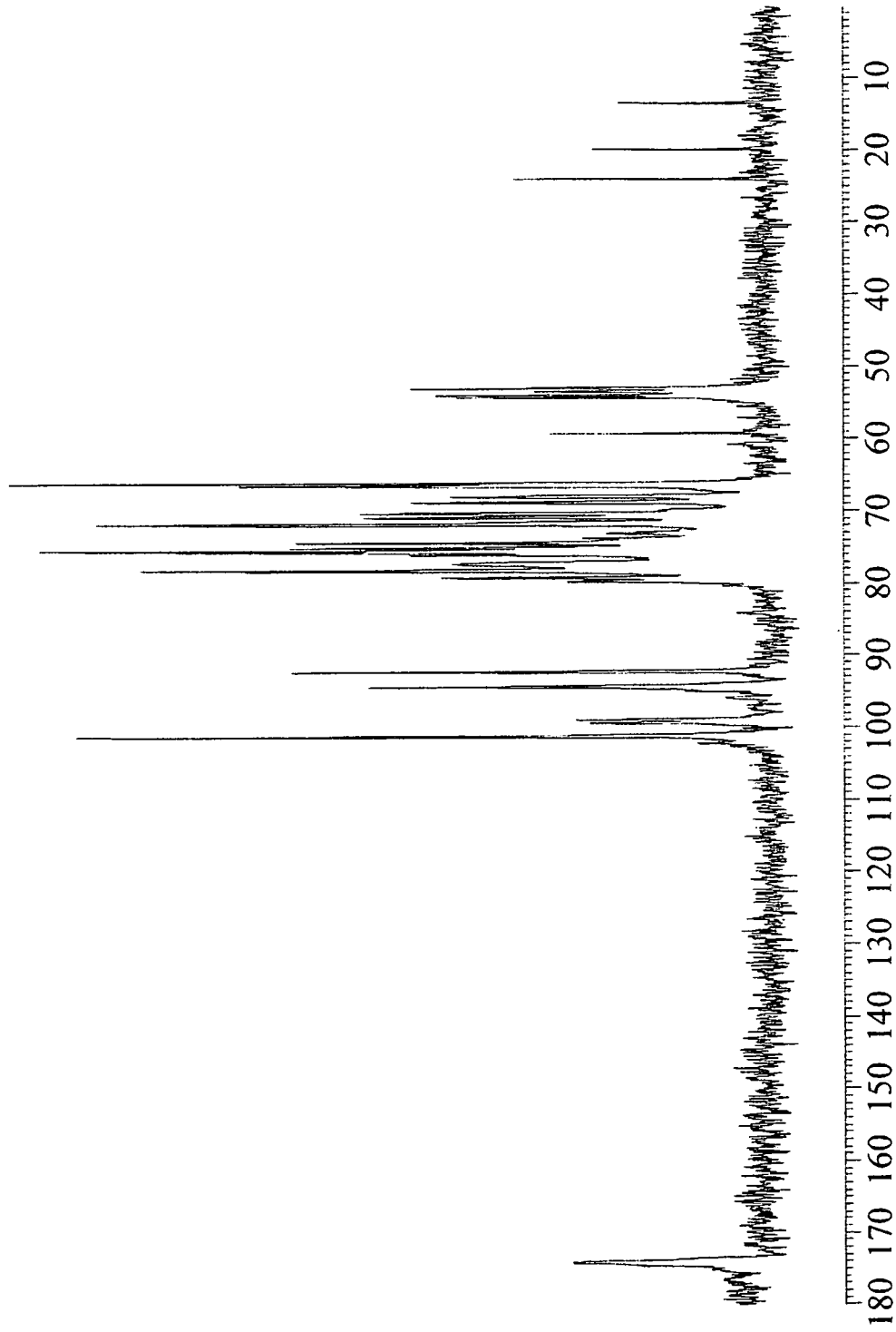
FIG. 7 shows the $^{13}$C-NMR spectrum, used to calculate the sulfate/carboxyl ratio of 3.55, of the epiK5-amine-O-oversulfate of Example 1(b).

A solution containing the 805 mg of the salt thus obtained in 30 ml of dimethyliformamide is heated at 55° C. and 30 ml of dimethylformamide containing 2.26 g of pyridine.$SO_3$ adduct are added thereinto. The reaction at 55° C. is continued overnight then 60 ml of water are added to the mixture. After neutralization with 1N NaOH, the product is precipitated with 3 volumes of acetone saturated with NaCl and set at 4° C. overnight. The precipitate is recovered by filtration on guch G4 and then ultrafiltered with 1000 D Millipore TFF system and dried at reduced pressure. 550 mg of epi-K5-amine-O-oversulfate are obtained having a content of iduronic acid of 54%, of glucosamine-6-O-sulfate of 100%, of glucosamine 3-O-sulfate of 60%, of monosulfate glucuronic acid of 10%, of monosulfate iduronic acid of 15%, the rest of the uronic units being disulfated, with a sulfation degree of 3.55 measured by NMR. Its $^{13}$C-NMR spectrum, used for calculating the sulfate/carboxyl ratio (sulfation degree), is shown in FIG. 7.

EXAMPLE 2

N-Acetyl-epiK5-amine-O-oversulfate

Figure 2:
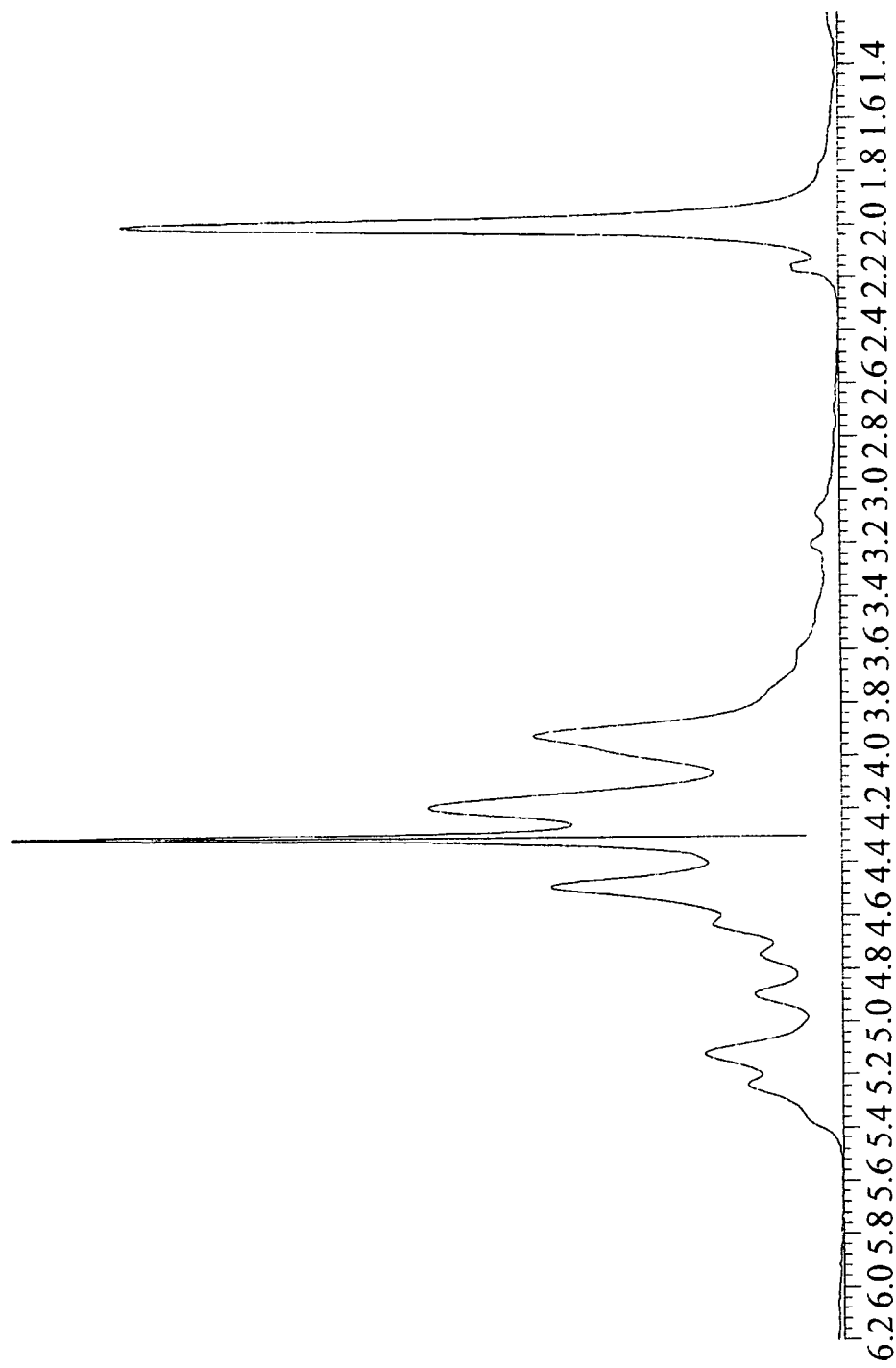
FIG. 2 shows the $^1$H-NMR spectrum of the N-acetyl-epiK5-amine-O-oversulfate of Example 2 with a sulfatecarboxyl ratio of 3.5.
Figure 5:
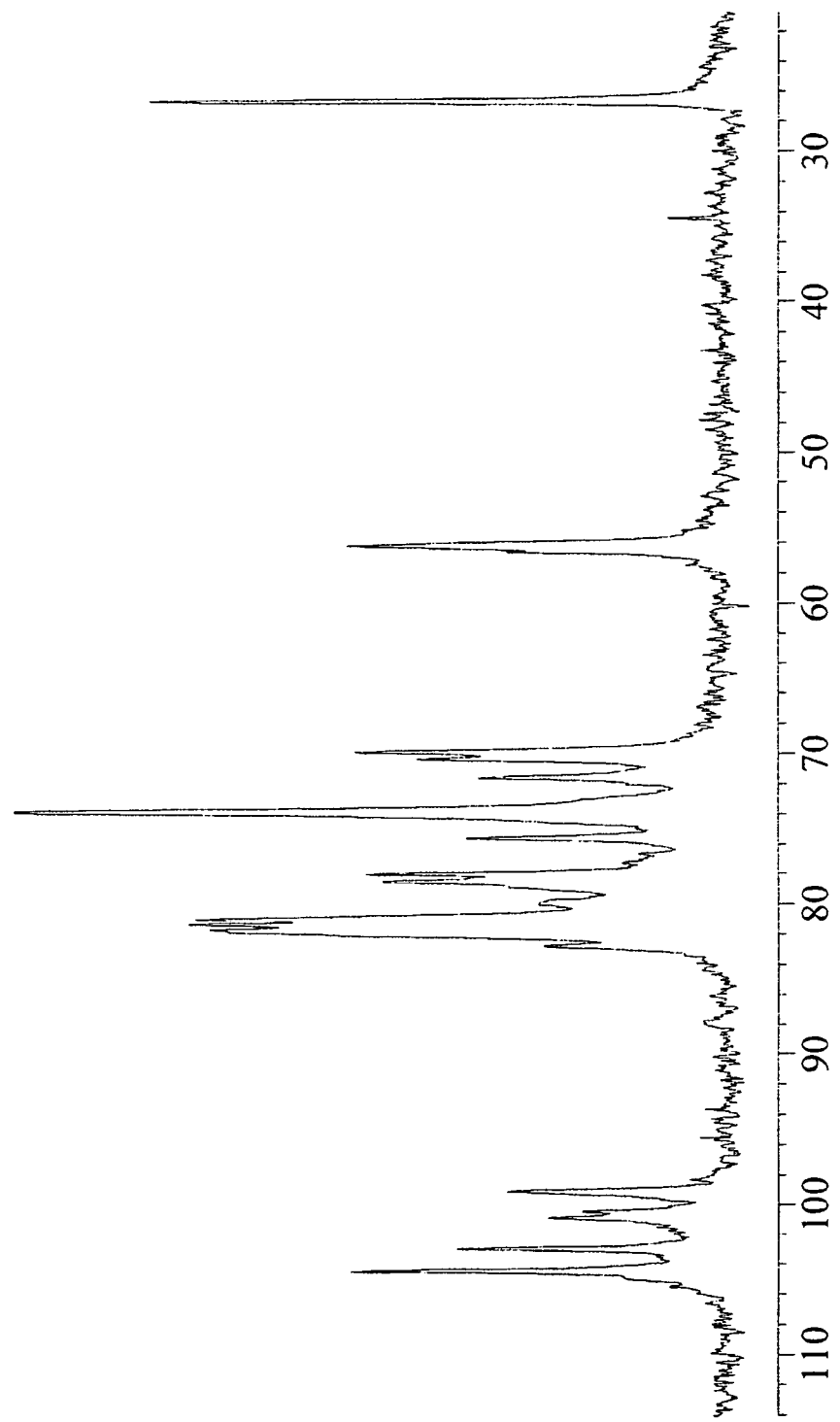
FIG. 5 shows the $^{13}$C-NMR spectrum of the N-acetyl-epiK5-amine-O-oversulfate of Example 2.

A volume of 7.5 ml of methanol and 3.75 ml of acetic anhydride is added to a solution of 250 mg of the epiK5-amine-O-oversulfate obtained in Example 1 in 75 ml of water, previously cooled to 4° C. The reaction is kept at 4° C. for 2 hours while maintaining the pH at a value of 7 with 5M NaOH. After ultrafiltration on 1,000 D membrane 3 volumes of acetone saturated with sodium chloride are added and the precipitate is recovered by centrifugation at 5,000 rpm for 5 min. Thus, 249 mg of N-acetyl-epiK5-amine-O-oversulfate are obtained with an iduronic acid content of 54%, glucosamine-6-O-sulfate of 100%, N-acetyl of 100%, glucosamine 3-O-sulfate of 60%, monosulfate glucuronic acid of 10%, monosulfate iduronic acid of 15%, the rest of the uronic units being disulfated, and whose sulfation degree is 3.5 measured with the conductimetric method according to Casu 1975. Its $^1$H-NMR spectrum is shown in FIG. 2. Its $^{13}$C-NMR spectrum is shown in FIG. 5.

By operating under identical conditions but substituting 3.54 ml of propionic anhydride for the amount of acetic anhydride, the corresponding N-propionyl-epiK5-amine-O-oversulfate is obtained.

EXAMPLE 3

N-acetyl-K5-amine-O-oversulfate (a) K5-amine-O-oversulfate

Figure 4:
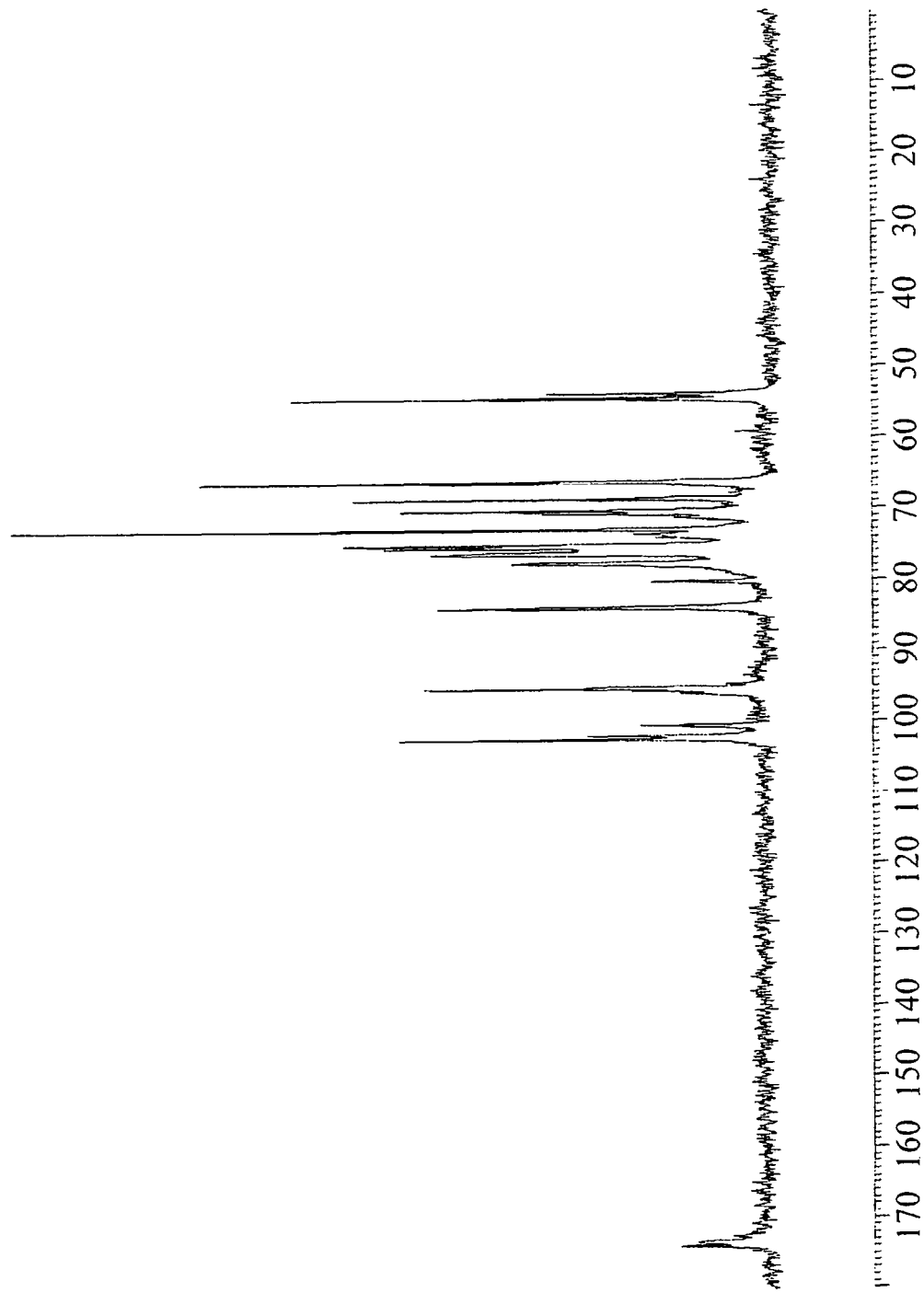
FIG. 4 shows the $^{13}$C-NMR spectrum, used to calculate the sulfate/carboxyl ratio, of the K5-amine-O-oversulfate of Example 3(a).

One g of K5-N,O-oversulfate obtained in Example 2 of WO/02068477, is dissolved in 200 ml of water and the solution is brought to pH 2 with 1 N HCl and thermostated at 50° C. The reaction is kept at 50° C. for 3 hours and then cooled to room temperature and neutralized with 1N NaOH. The product obtained is purified from salts by diafiltration using a 1,000 D cut off spiral membrane and isolated by freeze drying to give K5-amine-O-oversulfate. Its $^1$H-NMR spectrum is shown in FIG. 1. Its $^{13}$C-NMR spectrum, which a sulfation degree of 2.87 has been calculated from, is shown in FIG. 4.

(b) N-acetyl-K5-amine-O-oversulfate

Figure 3:
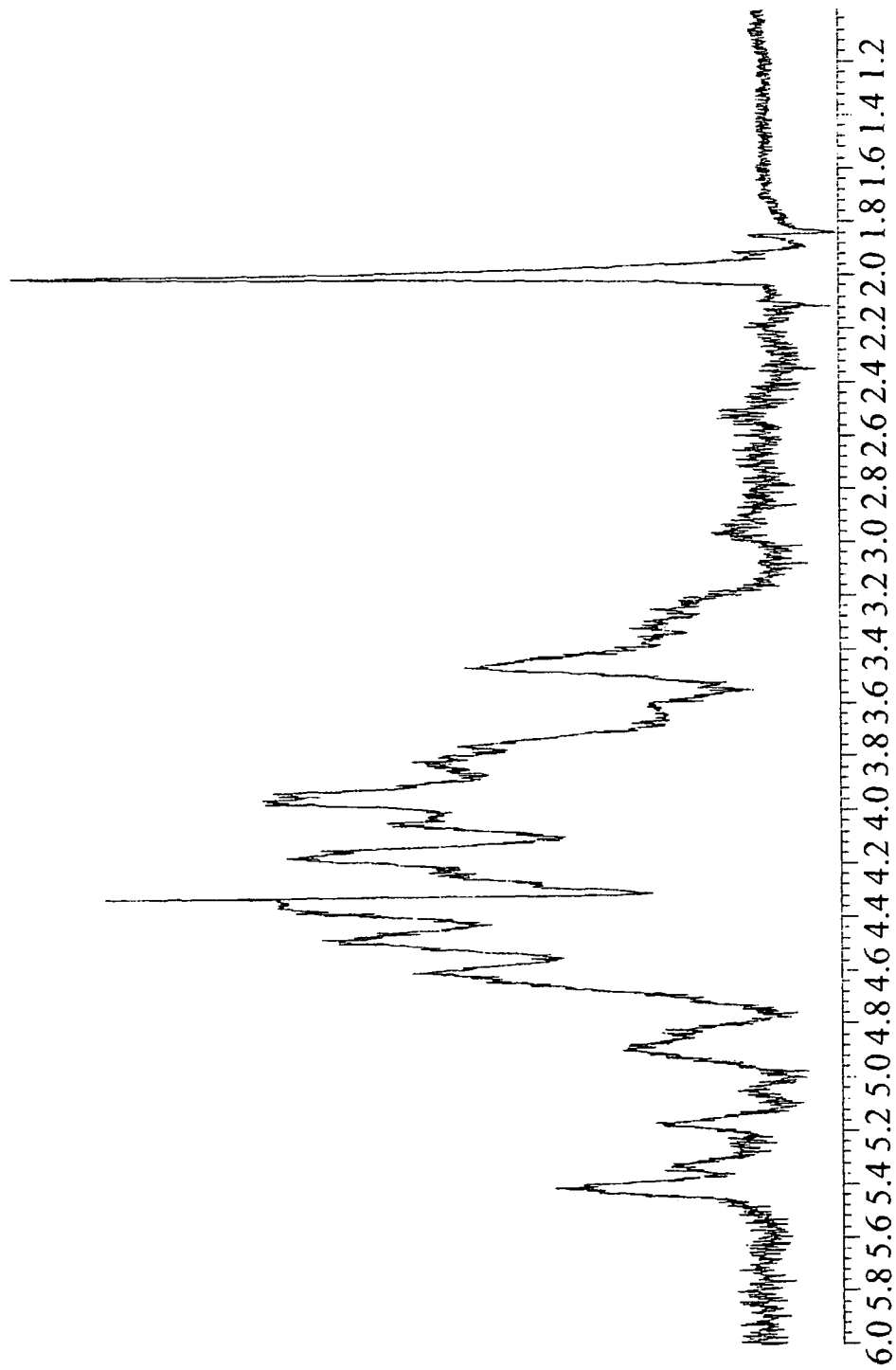
FIG. 3 shows the $^1$H-NMR spectrum of the N-acetyl-K5-amine-O-oversulfate of Example 3(b) with a sulfate/carboxyl ratio of 2.87.
Figure 6:
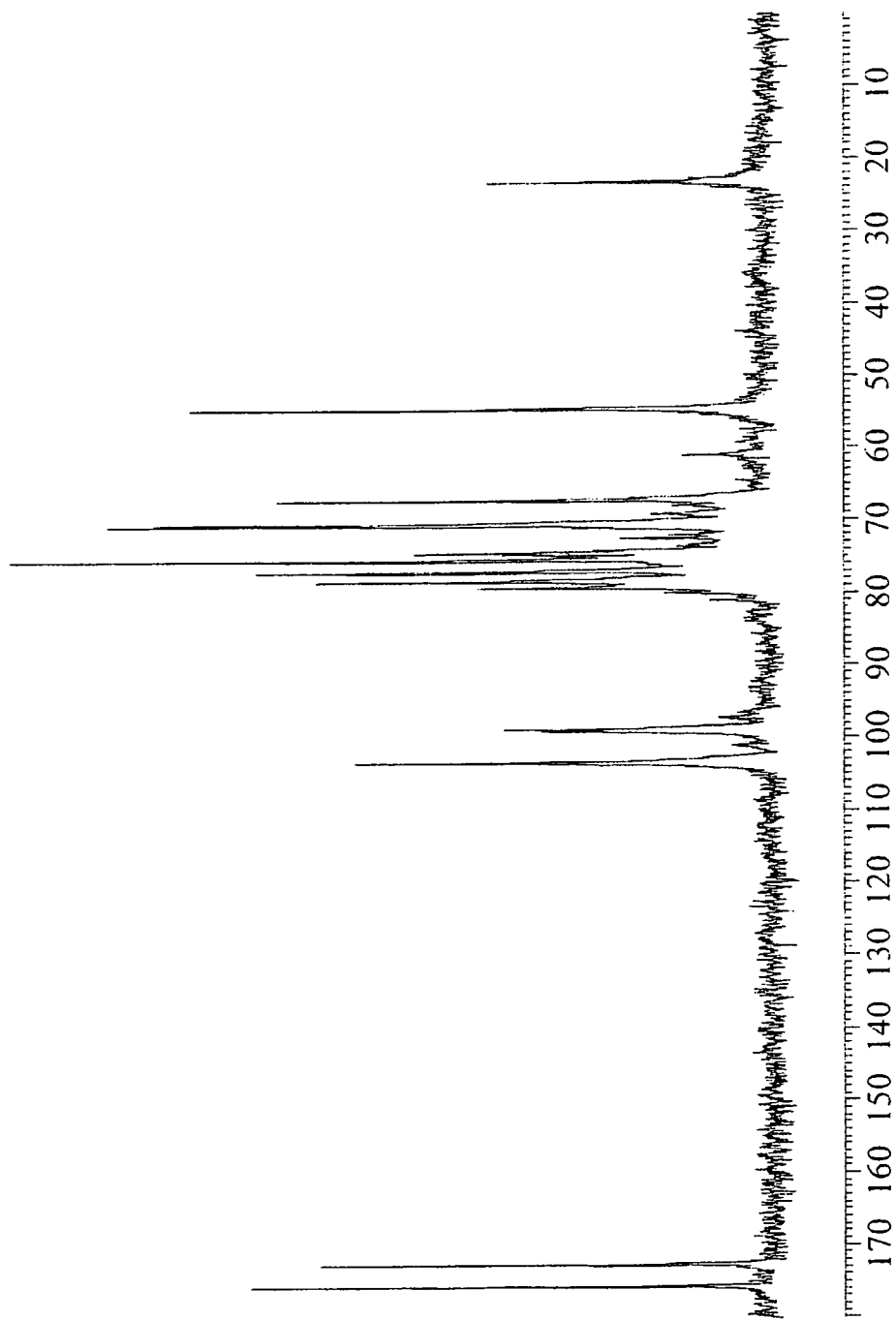
FIG. 6 shows the $^{13}$C-NMR spectrum of the N-acetyl-K5-amine-O-oversulfate of Example 3(b).

The K5-amine-O-oversulfate obtained in step (a) is dissolved in 20 ml of MeOH, the solution is then cooled to 4° C. and 10 ml of acetic anhydride are added thereinto. The reaction mixture is left at 4° C. for 2 hours maintaining the pH constantly at 7. At the end of the reaction the sample is purified from salts by ultrafiltration on a membrane with a 1000 D cut off and then recovered by dried at reduced pressure. A 100% N-acetylated product is obtained, 100% 6-0 sulfate, 30% monosulfate and 70% disulfate on the glucuronic acid is obtained. The $^1$H-NMR spectrum of the recovered N-acetyl-K5-amine-O-oversulfate is shown in FIG. 3. Its $^{13}$C-NMR spectrum is shown in FIG. 6. The sulfation degree (sulfate/carboxyl ratio) is 2.87. By operating under identical conditions but substituting 44.35 ml of butyric anhydride for the amount of acetic anhydride, the corresponding N-butyryl-K5-amine-O-oversulfate is obtained.

EXAMPLE 4

LMW-epiK5-amine-O-oversulfate Having a Mean Molecular Weight of 6,000

(a) Tetrabutylammonium Salt of the Depolymerized-LMW-epiK5-N-sulfate

A solution of 7 g of depolymerized-LMW-K5-N-sulfate obtained in PREPARATION VII in 350 ml water is passed through a column of IR-120 H$^+$. The pH of the eluate is 2.91. The percolated solution is brought to pH 7 with a 15% solution of tetrabutylammonium hydroxide (42.2 ml) and kept one hour at room temperature with controls in order to maintain the pH at a value of 7. After concentration on rotavapor of the tetrabutylammonium salt, the sample is frozen and lyophilized. Thus, 10.9 g of tetrabutylammonium salt of the depolymerized-LMW-epiK5-N-sulfate are obtained.

(b) O-Oversulfation

The tetrabutylammonium salt thus obtained is dissolved in 158 ml of dimethyl formamide, then 28.8 g of pyridine.SO$_3$ dissolved in 158 ml of DMF are added and the reaction mixture is kept at 45° C. for 18 hours. A volume of 316 ml water are added to stop the reaction and the pH is brought to 7 with 30% NaOH. The depolymerized-LMW-epiK5-amine-O-oversulfate is recovered by precipitation with 3 volumes of acetone saturated with NaCl (1.896 liters) and subsequent diafiltration on Millipore TFF 1,000 D membrane until elimination of the salts. The depolymerized-LMW-epiK5-amine-O-oversulfate has a mean molecular weight of 6,000.

All of the cited publications and patent documents are incorporated by reference herein.

What is claimed is:

1. An N-acyl-epiK5-amine-O-oversulfate-derivative, which is produced from an epiK5-N-sulfate-derivative, in which acyl is a (C$_2$-C$_4$)acyl, (3-methoxycarbonyl)propionyl, or (3-ethoxycarbonyl)propionyl, having an iduronic acid content of 20-60%, a mean molecular weight from approximately 2,000 to approximately 45,000 and a sulfation degree of at least 3.4, with a glucosamine 3-O-sulfate content of at least 40%, or one of its chemically or pharmaceutically acceptable salts.

2. The N-acyl-epiK5-amine-O-oversulfate-derivative according to claim 1, whose mean molecular weight is between approximately 15,000 and approximately 45,000.

3. The N-acyl-epiK5-amine-O-oversulfate-derivative according to claim 1, whose mean molecular weight is between approximately 4,500 and approximately 8,500.

4. The N-acyl-epiK5-amine-O-oversulfate-derivative according to claim 1, wherein said degree of sulfation is from 3.4 to 3.8.

5. The N-acyl-epiK5-amine-O-oversulfate-derivative according to claim 1 in which the substituent (C$_2$-C$_4$)acyl is selected from the group consisting of acetyl, (2-carboxy)acetyl, (2-methoxycarbonyl)acetyl, (2ethoxycarbonyl)acetyl, propionyl, and (3-carboxy)propionyl.

6. The N-acyl-epiK5-amine-O-oversulfate-derivative according to claim 1, wherein said salt is an alkaline metal or alkaline-earth metal, ammonium, (C$_1$-C$_4$)tetraalkylammonium, aluminum or zinc salt.

7. An N-acyl-epiK5-amine-O-oversulfate-derivative consisting of chain mixtures in which at least 90% of said chains have the formula IV

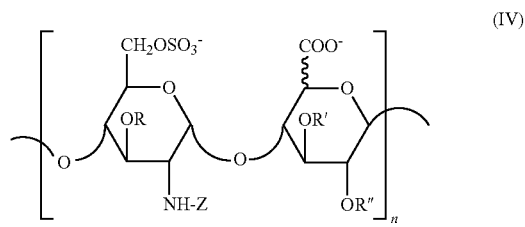

in which the uronic units are 20-60% consisting of iduronic acid, n is an integer from 2 to 100, R, R' and R" are hydrogen or SO$_3^-$, Z is (C$_2$-C$_4$) acyl, the degree of sulfation is at least 3.4 and the corresponding cation is chemically or pharmaceutically acceptable.

8. The N-acyl-epiK5-amine-O-oversulfate-derivative according to claim 7, consisting of a chain mixture in which at least 90% of said chains have the formula IV in which the uronic units are 40-60% consisting of iduronic acid, n is an integer from 3 to 100, with a mean molecular weight from approximately 2,000 to approximately 45,000, R is at least 40% SO$_3^-$, R' and R" are both SO$_3^-$ or one is hydrogen and the other is 5-10% SO$_3^-$ in monosulfate glucuronic acid and 10-15% SO$_3^-$ in monosulfate iduronic acid and the corresponding cation is chemically or pharmaceutically acceptable.

9. The N-acyl-epiK5-amine-O-oversulfate-derivative according to claim 8, which is a LMW-N-acyl-epiK5-O-oversulfate consisting of a mixture of chains wherein at least 90% of said chains have the formula IV'

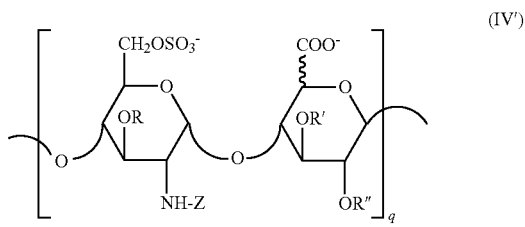

in which q is an integer from 2 to 20, R, R' and R" represent hydrogen or an $SO_3^-$ group for a degree of sulfation of from 3.55 to 4, Z is ($C_2$-$C_4$)acyl, bearing a sulphated 2,5-anhydromannitol unit of structure (a')

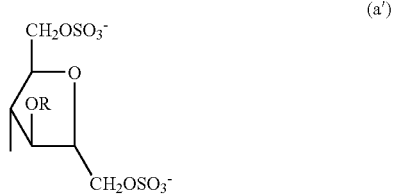

(a')

wherein R represent hydrogen or $SO_3^{31}$, in the majority of the chains in said mixture of chains, and the corresponding cation is chemically or pharmaceutically acceptable.

10. The LMW-N-acyl-epiK5-amine-O-oversulfate according to claim 9, consisting of a chain mixture in which the preponderant species is a compound of formula IV'a

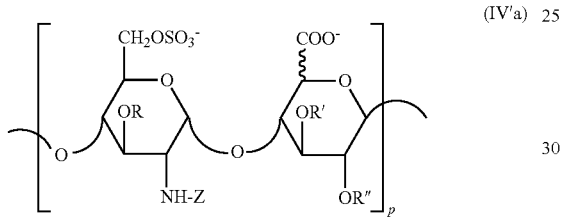

(IV'a)

in which p is an integer from 4 to 8, R, R' and R" are hydrogen or an $SO_3^-$ group for a degree of sulfation from 3.55 to 4, Z is ($C_2$-$C_4$)acyl, and the corresponding cation is chemically or pharmaceutically acceptable.

11. The LMW-N-acyl-epiK5-amine-O-oversulfate according to claim 10, wherein said preponderant species is a compound of formula IV'b

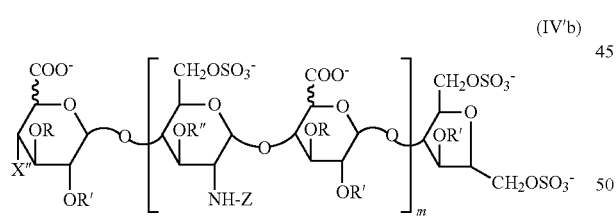

(IV'b)

in which R, R' and R" are hydrogen or $SO_3^-$, Z is ($C_2$-$C_4$) acyl, X" is OH or $OSO_3^-$, m is 4, 5 or 6, for a degree of sulfation from 3.55 to 4, the uronic units are present alternately, starting with a glucuronic or iduronic unit, and the corresponding cation is chemically or pharmaceutically acceptable.

12. A process for the preparation of N-acyl-epiK5-amine-O-oversulfate-derivative, which is produced from an epiK5-N-sulfate-derivative, in which acyl is a ($C_2$-$C_4$)acyl, having an iduronic acid content of 20-60%, a mean molecular weight from approximately 2,000 to approximately 45,000 and a sulfation degree of at least 3.4, with a glucosamine 3-O-sulfate content of at least 40%, or of its chemically or pharmaceutically acceptable salts, which comprises (a) treating an epiK5-N-sulfate-derivative, in acidic form, with a tertiary or quaternary organic base, letting the reaction mixture to stand for a time period of 30-60 minutes, maintaining the pH of the solution at a value of approximately 7 and isolating its salt with said organic base;

(b) treating said organic base salt of said (epi)K5-N-sulfate-derivative with an O-sulfation reagent in the conditions of O-oversulfation;

(c) treating the epiK5-amine-O-oversulfate-derivative thus obtained with a functional derivative of a ($C_2$-$C_4$) carboxylic acid and isolating the N-acyl-epiK5-amine-O-oversulfate-derivative or a salt thereof.

13. The process according to claim 12, wherein said N-acyl-epiK5-amine-O-oversulfate-derivative is isolated in sodium salt form and optionally transformed into another chemically or pharmaceutically acceptable salt.

14. The process according claim 12, wherein, in step (a) tetrabutylammonium hydroxide is used as an organic base.

15. The process according to claim 12, wherein in step (b) the O-oversulfation is carried out in dimethylformamide utilizing 2-4 moles of O-sulfation reagent per available OH per disaccharide at a temperature of 40-60° C. for 15-20 hours.

16. The process according to claim 12, wherein as starting material an epiK5-N-sulfate-derivative is used having a mean molecular weight from approximately 1,000 to approximately 25,000.

17. The process according to claim 16, wherein said starting material has an iduronic acid content of 40-60%.

18. The process according to claim 16, wherein said starting material has a mean molecular weight from approximately 1,500 to approximately 25,000.

19. Process according to claim 18, wherein said starting material has a mean molecular weight between 10,000 and 25,000.

20. The process according to claim 18, wherein said starting material has a mean molecular weight from approximately 1,500 to approximately 12,000.

21. The process according to claim 20, wherein said starting material has a mean molecular weight from approximately 1,500 to approximately 8,000.

22. The process according to claim 12, wherein as starting material an epiK5-N-sulfate-derivative is used consisting of a chain mixture in which at least 90% of said chains have the formula I

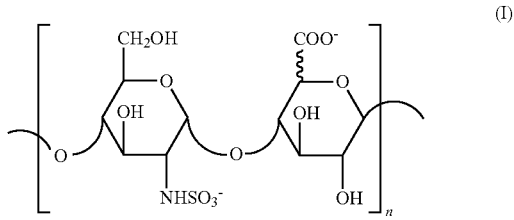

(I)

in which n is an integer from 2 to 100 and the corresponding cation is chemically or pharmaceutically acceptable.

23. The process according to claim 22, wherein said starting material consists of a chain mixture in which at least 90% of said chains have the formula I, in which the uronic units are 40-60% consisting of iduronic acid.

24. The process according to claim 22, wherein said starting material is a LMW-epiK5-N-sulfate consisting of a chain mixture in which at least 90% of said chains have the formula I in which n is an integer from 3 to 15 and the corresponding cation is chemically or pharmaceutically acceptable.

25. The process according to claim 22, wherein said starting material is a LMW-epiK5-N-sulfate consisting of a chain mixture in which at least 90% of said chains have the formula I'

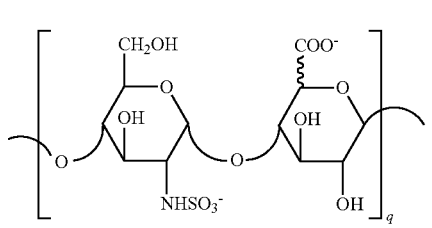

(I')

in which q is an integer from 2 to 20 and the corresponding cation is chemically or pharmaceutically acceptable.

26. The process according to claim 22, wherein said starting material is a LMW-epiK5-N-sulfate consisting of a chain mixture in which the preponderant species has the formula I'a

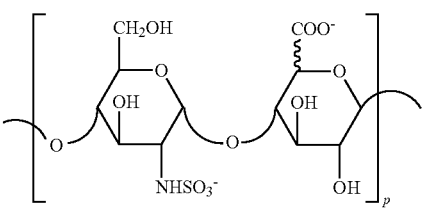

(I'a)

in which p is an integer form 4 to 8.

27. The process according to claim 16, wherein said starting material is a LMW-epiK5-N-sulfate obtained by nitrous depolymerization of the corresponding epiK5-N-sulfate and subsequent reduction.

28. The process according to claim 27, wherein said starting LMW-epiK5-N-sulfate contains, at the reducing end of the majority of the chains in said chain mixture, a 2,5-anhydromanno unit of structure (a)

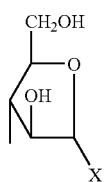

(a)

in which X represents a hydroxymethyl group.

29. The process according to claim 27, wherein as starting material a LMW-epiK5-N-sulfate is used consisting of a mixture of chains in which the preponderant species is a compound of formula I'b

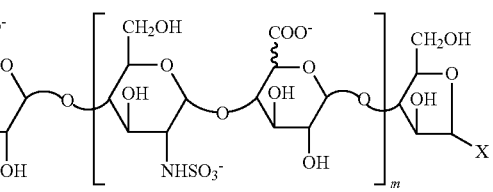

(I'b)

in which X represents a hydroxymethyl group, m is 4, 5 or 6 and the corresponding cation is chemically or pharmaceutically acceptable.

30. The process according to claim 12, wherein said starting epiK5-N-sulfate-derivative is utilized in sodium salt form.

\* \* \* \* \*